United States Patent [19]
Eppstein et al.

[11] Patent Number: 6,045,502
[45] Date of Patent: Apr. 4, 2000

[54] ANALYZING SYSTEM WITH DISPOSABLE CALIBRATION DEVICE

[75] Inventors: Jonathan A. Eppstein, Atlanta; Mark A. Samuels, Norcross; Keith D. Ignotz, Duluth; Gregory J. Newman, Atlanta, all of Ga.

[73] Assignee: SpectRx, Inc., Norcross, Ga.

[21] Appl. No.: 08/904,766

[22] Filed: Aug. 1, 1997

Related U.S. Application Data

[63] Continuation-in-part of application No. 08/621,182, Mar. 21, 1996, abandoned, which is a continuation-in-part of application No. 08/587,949, Jan. 17, 1996, Pat. No. 5,860,421.

[51] Int. Cl.[7] ..................................................... A61B 5/00
[52] U.S. Cl. ........................................... 600/306; 600/315
[58] Field of Search ...................... 178/18.09; 250/491.1; 73/620, 621; 378/18, 207; 356/243, 244; 600/306, 309, 310, 473, 476, 477, 315

[56] References Cited

U.S. PATENT DOCUMENTS 4,029,085  6/1977  DeWitt et al. ........................... 600/315
5,353,790  10/1994  Jacques et al. .......................... 600/315
5,792,049  8/1998  Eppstein et al. ........................ 600/306

*Primary Examiner*—George Manuel
*Attorney, Agent, or Firm*—Fleshner & Kim

[57] ABSTRACT

A system and method for calibrating a measurement instrument prior to making a measurement on a material or tissue includes utilizing a removable calibration device to calibrate the instrument, then removing a target portion of the calibration device so that a measurement may be performed. The calibration device may include an index matching agent, such as a gel, that is to be interposed between the patient's skin and an output end of the measuring instrument. A method embodying the invention may include making a bilirubin concentration measurement on a skin of a patient by measuring the amplitude of light reflected from the patient's skin at first and second wavelengths indicative of a blood content of the patient's skin, and measuring the amplitude of reflected light at a third wavelength indicative of an uncorrected bilirubin concentration, then calculating a corrected bilirubin concentration based on the three measurements. The method may also include taking measurements at fourth and fifth wavelengths indicative of a melanin content of the patient's skin, and calculating the bilirubin concentration based on the fourth and fifth measurements.

49 Claims, 30 Drawing Sheets

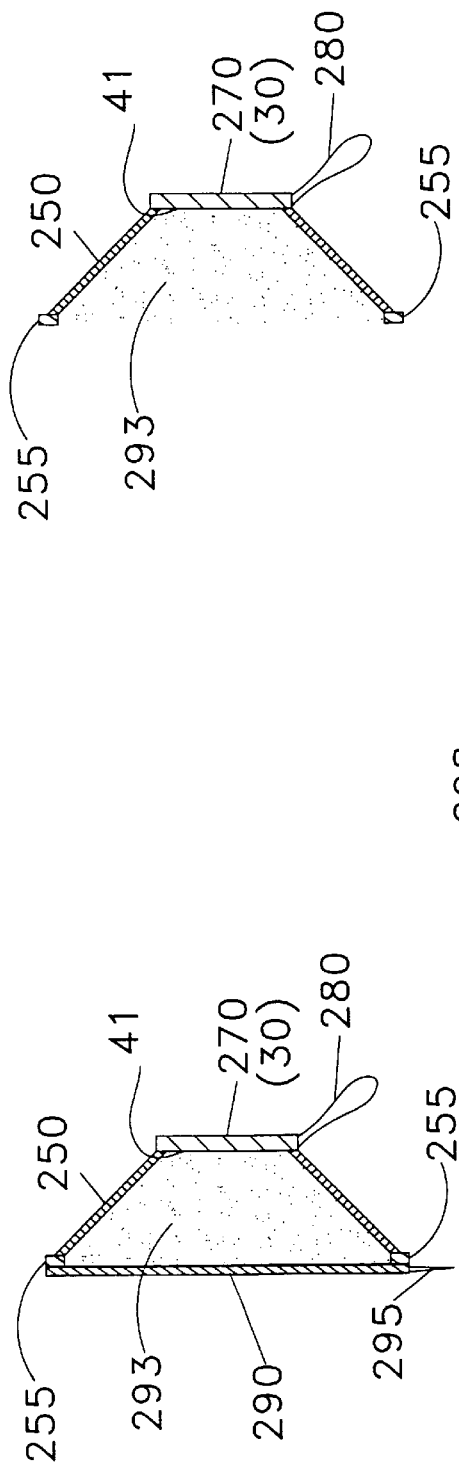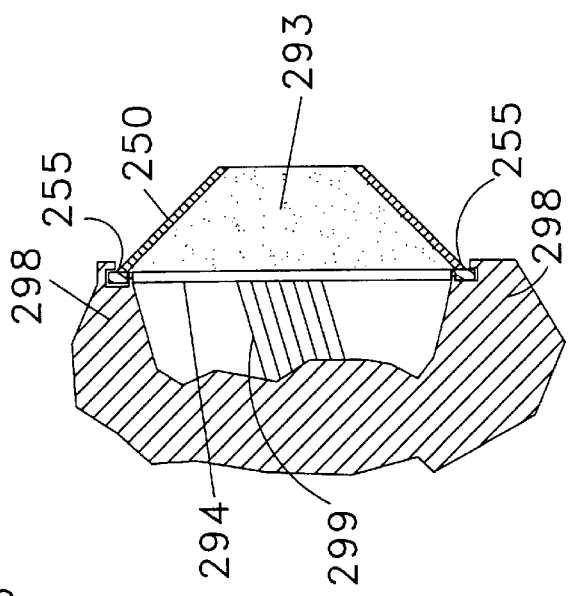

ANALYZING SYSTEM WITH DISPOSABLE CALIBRATION DEVICE

RELATED APPLICATIONS

This application is a continuation-in-part of the U.S. patent application Ser. No. 08/621,182, entitled "SPECTROSCOPIC SYSTEM WITH DISPOSABLE CALIBRATION DEVICE," filed Mar. 21, 1996, now abandoned, which in turn is a continuation-in-part of U.S. patent application Ser. No. 08/587,949, entitled "APPARATUS AND METHOD FOR CALIBRATING MEASUREMENT INSTRUMENTS", filed on Jan. 17, 1996 now U.S. Pat. No. 5,860,421. The contents of both applications are hereby incorporated by reference.

BACKGROUND OF THE INVENTION

1. Field of the Invention

This invention relates to instruments that require calibration to make measurements on animal tissues or other materials, and in particular, to measurement instruments that utilize a removable calibration device that ensures proper calibration of the measurement instrument. The calibration device includes a removable calibration target that ensures proper calibration of the measurement instrument. The calibration device may be disposable, and the measurement instrument may prevent reuse of the disposable calibration device, thereby helping to control the spread of infection if the measurements are made on tissues, and helping to prevent contamination if the measurements are made on materials. The invention also relates to apparatus and methods of determining a bilirubin concentration in a human's blood.

2. Background of the Related Art

Spectroscopy is currently used for a wide variety of purposes including evaluation of in-vivo or in-vitro tissue samples. One type of spectroscopy, reflectance spectroscopy, involves diffusely reflecting light from tissue, non-invasively, and analyzing the reflected light. Such spectroscopic devices must be calibrated prior to use, especially when made for medical or other critical applications. Instrument calibration can be affected by variations in light source intensity, spectral characteristics, lens-aging, lens cleanliness, to temperature, detector sensitivity changes, and electronic drifting.

More generally, there has been an increase in the use of light as a diagnostic tool in many areas of medicine. This development has become more pervasive with the development of appropriate and inexpensive light sources, detection devices and optical fibers that allow for minimal invasiveness.

Typically, spectral transmittance, fluorescence (normal and time resolved) and Raman spectroscopy are used to evaluate biological tissues and other materials in order to determine the materials present and to measure their concentrations. These methods are affected by the scattering, reflecting, absorbing and transmitting properties of the instrument optics, detectors, sources and the media under examination. This is due to the fact that the amount of light reaching the tissue to be measured is a function of those parameters, and in the case of fluorescence and Raman emissions, re-absorption of emission spectra.

Acoustic type measuring systems are also used for a wide variety of purposes including to evaluate tissue or materials. Acoustic measurement systems also experience variations in the output energy of the acoustic wave source, changes in spectral characteristics of the tissue or material due to changes in temperature, detector sensitivity changes, and electronic drifting.

Many of the above-described types of measurement systems require calibrations to be performed on a routine basis in order to compensate for changes in instrument performance and response. This is true for both radiation based measurement systems, i.e., systems that reflect electromagnetic radiation from the tissue or material to be measured and then analyze the return radiation, and acoustic based measurement systems, i.e., systems that reflect acoustic waves or energy from the tissue or material to be measured and then analyze the return acoustic signal.

Calibration techniques typically involve measuring the response of a test target with characteristics that remain stable over time and over a range of temperatures. Those calibration techniques can also be used to compensate for instrument to instrument variations, and for any changes that an individual instrument may experience over its working lifetime.

Although others have proposed calibration fixtures that compensate for these variations in instrument performance, none have provided a simultaneous solution to both the calibration issue and the problems associated with the spread of infection in a medical setting. Furthermore, calibration devices that are designed to be reused can become damaged by sunlight, temperature, humidity and other effects, which could lead to errors in calibration.

Various types of calibration techniques and devices have been attempted. For example, U.S. Pat. No. 5,365,925 describes a calibration boot which includes a plurality of materials, which is placed over an optical catheter for the purpose of making a multi-point calibration of reflected or backscattered light. U.S. Pat. No. 5,311,273 describes a method of using four black body radiators to provide calibration of an infrared spectrometer. However, neither of these approaches involves an inexpensive calibration target that can be easily discarded after each use. In addition, neither of these systems prevent a user from taking a measurement without going through a calibration step.

U.S. Pat. No. 4,981,355 describes a calibration device for the in vitro calibration of a light guide, whereby a polyethylene material has a plurality of light scattering particles and a plurality of light absorbing particles which yields a neutral density filtering type of effect, uniformly distributing light in the plastic parts of the calibrator. The calibrator can be positioned into a sterile tray which is protected by a tear off plastic. Once the calibration is complete, the surgeon removes the catheter from the calibrator and the tray in which it is held and then presumably disposes of the calibration device and its tray. This approach, however, is neither simple nor inexpensive.

U.S. Pat. No. 4,796,633 describes a calibration reference apparatus that fits over a light guide. A stop limits the extent to which the light guide can be advanced into the cavity, whereby an endface of the light guide is spaced from a region of the surface to define a gap. The end wall and the gap are adapted to return a known ratio of the light directed into the gap from the end face of the light guide. Again, however, this approach does not involve an inexpensive, disposable calibration device.

U.S. Pat. No. 4,744,656 discloses a calibration boot that snaps into place over an optical catheter allowing calibration of the catheter before use. Once the calibration is complete, the boot is removed and the optical catheter is ready for use. Each new catheter comes with a new boot. However, the boot is not present during the measurement and there is no provision to prevent reuse of the boot.

One application of spectroscopic systems involves detection of a bilirubin concentration in a human. Bilirubin is produced from the breakdown of hemoglobin in red blood cells. Under normal conditions, the bilirubin is conjugated by glucoronyl transferase, an enzyme present in the liver, and is then excreted through the biliary system.

Newborn infants and prematurely born infants are particularly susceptible to hyperbilirubinemia. Hyperbilirubinemia describes the state where there is excessive bilirubin in the body. Often this is due to the lack of functioning glucoronyl transferase enzyme in their liver, or excessive red blood cell breakdown associated with erythroblastosis fetalis.

One method for bilirubin testing includes blood based lab assay testing. The "heel stick" blood lab assay is currently the only accepted methodology for quantitative bilirubin testing results in the United States. Of course, this invasive approach requires that blood be drawn to perform the test.

Non-invasive measurements of the bilirubin concentration would eliminate the need to draw blood samples from patients for bilirubin analysis. It would also provide easy patient interface. It is known that bilirubin can be measured non-invasively by taking reflectance measurements from a patient's skin, from the aqueous of the eye, or from the sclera (white) of the eye, based on the fluorescent signature. Reflectance measurements can also be made on the tympanic membrane of the ear. This is possible because bilirubin from the blood stains the skin as well as other tissues of the body. Jaundice refers to the condition when the bilirubin is visible in the skin and sclera.

Many attempts have been made to measure cutaneous bilirubin non-invasively. These attempts include the development of visual reference standards, and transcutaneous reflectance spectroscopy to measure the absorption spectra of bilirubin, oxidized blood, and melanin, the dominant absorbers in the skin. The concentration of these pigments have distinct absorption spectra.

Reflectance bilirubinometers have obtained reasonable correlations between bilirubin levels determined transcutaneously and serum bilirubin concentrations in homogeneous patient populations. Unfortunately, these devices have failed to give satisfactory correlations when used over a heterogeneous population. Since patient populations are rarely homogeneous, transcutaneous bilirubin measuring methods have not been widely accepted clinically.

One known system, which implements a non-invasive cutaneous testing approach for bilirubin and is in wide use in Japan, is the Minolta Jaundice Meter. That approach, however, has not been approved for use in the United States, although it is used for screening purposes in some U.S. institutions. In addition, that approach does not account for variations in skin color and thickness.

Another approach to testing for bilirubin that does not require the drawing of blood is a breath analysis approach introduced by a group from Stanford. This approach does not have a quantitative accuracy required to have a high correlation to serum bilirubin. Hence, it appears to only have potential use as a screening technique.

SUMMARY OF THE INVENTION

An object of the invention is to provide a measurement system with a disposable calibration device that is inexpensive and that helps to prevent contamination or infection.

Another object of the invention is to provide a spectroscopic system which uses a calibration device which provides an optically clear, scratch-free window between the optical instrument and the tissue or material to be measured.

Another object of the invention is to provide a simple and accurate apparatus and method of measuring a patient's bilirubin concentration.

One advantage of a measuring system embodying the invention that uses a disposable calibration device is that once used, the calibration device cannot be re-used, thereby reducing the risk of infection or contamination.

Another feature of the invention is that the disposable calibration device can include a calibration target having a user graspable tear tab which allows the calibration target to be easily removed from the calibration device without disturbing an underlying window of a measurement instrument.

Another feature of the invention is that the calibration device can include a deflectable outer annulus which comes into contact with the tissue or material to be measured, the annulus deflecting as the instrument is brought close to a material or tissue, the deflection enabling the instrument to take a measurement.

Another feature of the invention is that a measurement instrument embodying the invention, that utilizes electromagnetic radiation, may include one or more transmit and receive fiber optic waveguides for directing electromagnetic radiation to a material or tissue to be measured and for conducting reflected or dispersed radiation back to a sensor of the instrument. The instrument may be configured such that radiation transmitted from the instrument toward the material or tissue being measured is directed toward the material or tissue at an angle relative to a plane normal to the surface of the material or tissue so as to reduce backscattering effects.

Another feature of the invention is that a calibration device embodying the invention may include an index matching substance, such as a gel, that can be interposed between a material or tissue being measured and a distal end of a measurement instrument.

Another feature of the invention is that a measurement instrument designed to measure a bilirubin concentration in a patient may accomplish the measurement using the amplitude of radiation reflected from a patient's skin at first and second wavelengths representing a blood content of the skin, and at a third wavelength representing an uncorrected bilirubin concentration. Such an instrument may also utilize the amplitude of reflected radiation at fourth and fifth wavelengths that represent a melanin content of the patient's skin.

These and other objects, advantages and features are accomplished by the provision of a measuring instrument that includes a radiation analyzer that transmits radiation to a material or tissue in order to effect measurements and that receives and analyzes radiation reflected from or dispersed from a material or tissue being measured. Alternatively, an instrument embodying the invention may emit, receive and analyze acoustic energy. The instrument may include a calibration device holder for holding a calibration device that includes a structure through which the radiation or acoustic energy can be transmitted, and that includes a removable calibration target arranged on said structure and capable of returning a portion of said radiation or acoustic energy for calibrating the instrument. The removable calibration target is removable from said structure to allow a measurement to be made on a material or tissue.

In one approach, the measuring instrument could include a window through which radiation or acoustic energy can pass as the radiation or acoustic energy travels from an emitter, to a material or tissue being measured, and back to a sensor. The structure and/or window can comprise a barrier or infection shield between the material or tissue and the measuring instrument.

A measuring instrument embodying the invention may comprise a spectrometer capable of determining the amplitude of radiation at any of a plurality of wavelengths. Alternatively, the measuring instrument may comprise a detector and one or more filters for selectively focusing radiation of specified wavelengths upon the detector. The measuring instrument could also comprise a plurality of filters and a corresponding plurality of detectors, where reflected radiation passes through the filters and onto the detectors so that each detector receives radiation at a different wavelength. The measuring instrument might also comprise a defraction grating and a plurality of detectors, wherein the defraction grating focuses radiation of predetermined wavelengths on respective ones of the plurality of detectors. Still further, the radiation analyzer may comprise a radiation detector and a linear variable filter.

A method of determining a bilirubin concentration of a patient that embodies the invention can include measuring the amplitude of reflected radiation at first and second wavelengths to determine a blood content of the patient's skin, measuring an amplitude of radiation at a third wavelength to determine an uncorrected bilirubin concentration of the patient, and analyzing the data to determine a corrected bilirubin concentration. A method embodying the invention may also include the step of measuring the amplitude of reflected radiation at fourth and fifth wavelengths to determine a melanin concentration in the patient's skin and analyzing the amplitudes of the first, second and third frequencies in light of the detected melanin concentration.

BRIEF DESCRIPTION OF THE DRAWINGS

FIG. 2C shows a schematic sectional representation of another calibration device for use with the measurement instrument;

FIG. 2D is a schematic representation of the calibration device of FIG. 2C wherein a removable seal has been peeled away from the calibration device;

FIG. 2E shows a schematic representation of the calibration of FIG. 2C mounted on a measurement instrument wherein a calibration target has been removed;

DETAILED DESCRIPTION OF PREFERRED EMBODIMENTS

A spectrometer system that uses a disposable calibration device for calibration will be described with reference to FIGS. 1A and 1B.

Figure 1A:
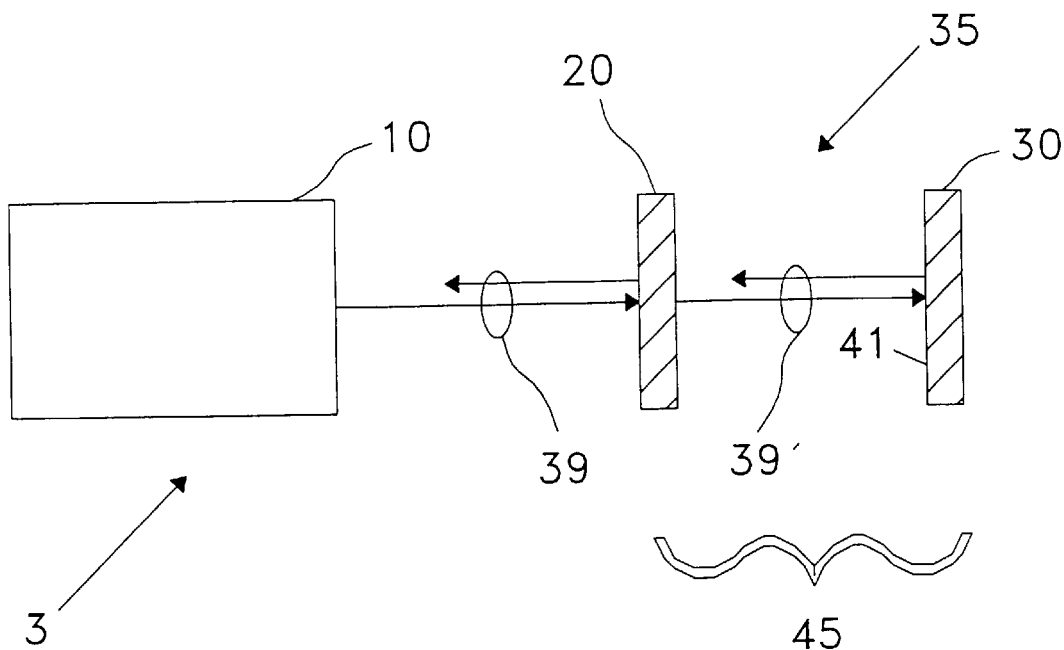
FIG. 1A shows a schematic view of a measurement system in a calibration mode.

FIG. 1A is a schematic view of a measurement system 3 in a calibration mode. The system 3 includes an instrument 10 which outputs electromagnetic radiation 39 and receives and analyzes radiation reflected back towards the device by a material or tissue being measured. Alternatively, the instrument 10 may output, receive and analyze acoustic waves. Reference number 39 will be used to represent electromagnetic radiation or acoustic waves just as reference number 10 will be used to represent an instrument that outputs either electromagnetic radiation or acoustic waves. If the instrument 10 outputs electromagnetic radiation 39, that radiation can lie within the visible, infrared, ultra-violet regimes, and/or within the rf, microwave and millimeter wave regimes. With regard to electromagnetic radiation 39, the instrument 10 can be a spectrometer, laser radar, radar or any other radiation measuring instrument that outputs radiation to a material or tissue 40, then measures some portion of the return signal. With regard to acoustic waves, the instrument 10 can be an acoustic measuring/imaging device that outputs acoustic waves and measures the return acoustic wave signal. The discussion that follows is drawn to a device that uses electromagnetic radiation, it being understood that an analogous discussion applies for an instrument that uses acoustic waves.

During a calibration procedure, as shown in FIG. 1A, radiation 39 is transmitted toward and through a shield 20 toward a calibration target 30. The shield 20 serves as a barrier between the instrument 10 and a material or tissue 40 to be measured, and hence functions to reduce contamination of the material or tissue 40. One major (but not the only) purpose of the shield 20 is to guard against possible infection when living tissue 40 is measured. Hence, the shield 20 might also be referred to as an infection shield. A shield 20 must be at least partially transmissive to radiation 39 such that a portion of the emitted radiation passes through the window 20 to appear as radiation 39.

Radiation 39' passes through a region 35 and reaches a surface 41 of the calibration target 30. The surface 41 can be the same material as the calibration target 30, or a specially applied layer. The surface 41 reflects or scatters radiation back towards the instrument 10. Note that throughout this specification, reflection and scattering are used interchangeably and are meant to indicate that radiation travels back toward instrument 10. Also, region 35 can include a variety of adhesives, gels, pastes, or other materials. Once system 3 with instrument 10 is calibrated, calibration target 30 is removed, and system 3 is now ready to take measurements on material 40 through shield 20.

Figure 1B:
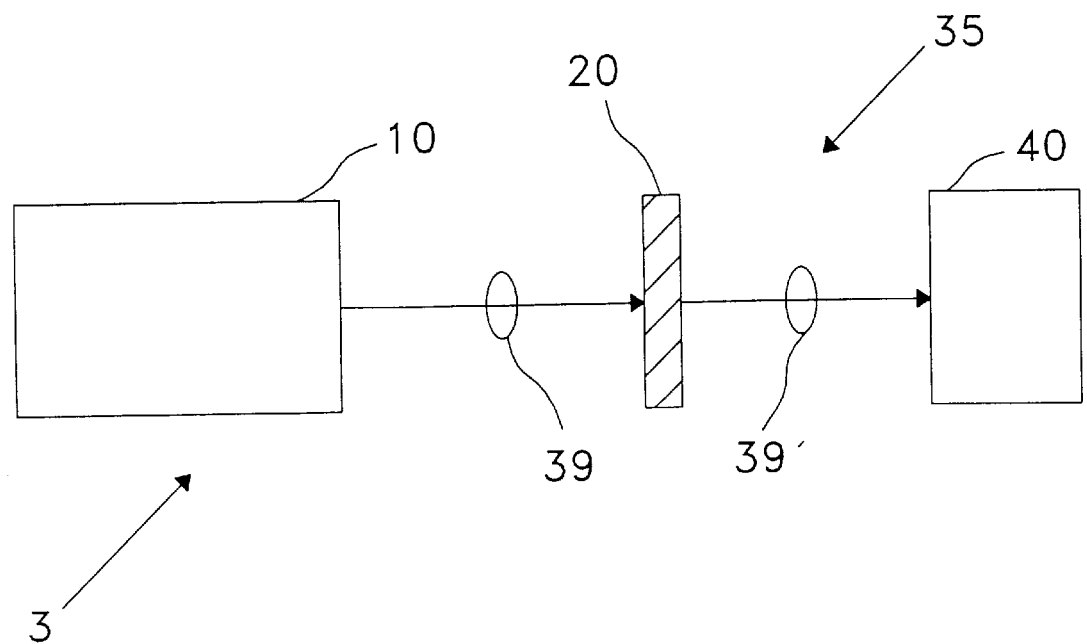
FIG. 1B shows a measurement system in a measurement mode wherein a calibration target has been removed and radiation is reaching a tissue or material to be measured.

FIG. 1B shows the system 3 in a measurement mode wherein calibration target 30 has been removed and radiation 39' is now reaching a tissue or material 40 to be measured through the shield 20.

Figure 2A:
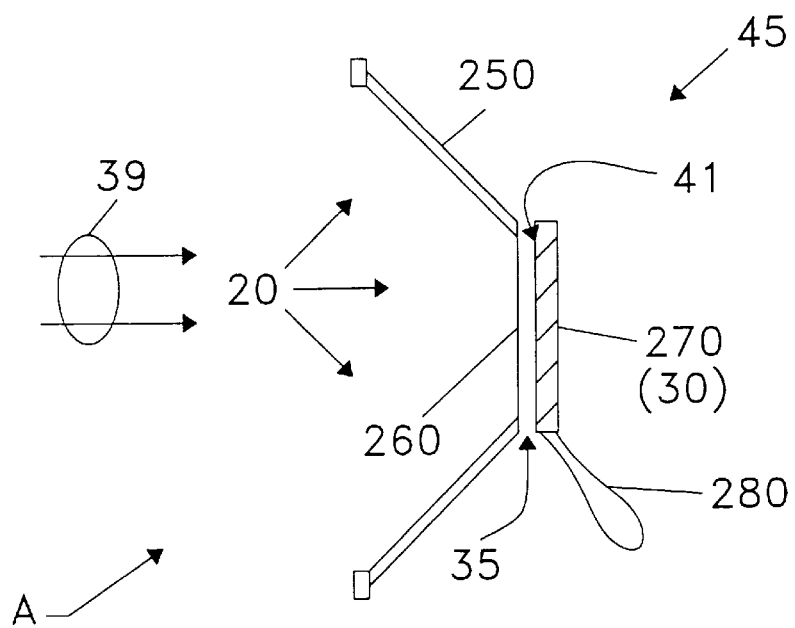
FIG. 2A shows a schematic representation of an embodiment of a calibration device for use with a measurement instrument.

FIG. 2A shows a schematic representation of a calibration device 45 embodying the invention. Device 45 includes a shield supporting structure 250 with a window 260. Together, the structure 250 and the window 260 comprise the shield 20 shown in FIG. 1A. In an alternative embodiment, window 260 can simply be an opening in the structure 250 and the discussion regarding the window 260 should be read to encompass either an opening or a structure, where appropriate. Also, in this embodiment, the supporting structure 250 has a cone-type shape with a cut off top 265 and a window 260 that is circular shaped and is arranged to cover the top 265. It should be understood, however, that the shape of the shield structure 250 need not be limited to a cone-type shape, and the window 260 need not be limited to a circular shape. Finally, the calibration device 45 includes a calibration target 270 (corresponding to the calibration target 30 from FIG. 1A) with a user graspable tab 280.

The calibration device 45 receives radiation 39 from an instrument 10. The radiation 39 passes through the window 260 and region 35 and reaches surface 41 of the calibration target 270. The window 260 must be at least partially (and preferably nearly completely) transparent to the radiation 39. The region 35 can include an adhesive, gel, liquid and/or free space. In one embodiment, the window 260 is statically charged with respect to surface 41 of calibration target 270. The static charge holds the calibration target 270 in place. Radiation 39 is then incident on the surface 41 of the calibration target 270.

The calibration target 270 should be selected to have a known reflection spectrum for calibration purposes (note that the radiation 39 is scattered or reflected from the calibration target 270 back towards the instrument 10). For instruments 10 which perform measurements of intensity, independent of wavelength, a highly reflective surface 41 of the calibration target 270 may be advantageous. This might include radar, laser radar and interferometric type instruments. Note, however, that such instruments might also benefit from using a less reflective surface 41 on the calibration target 270.

Figure 2B:
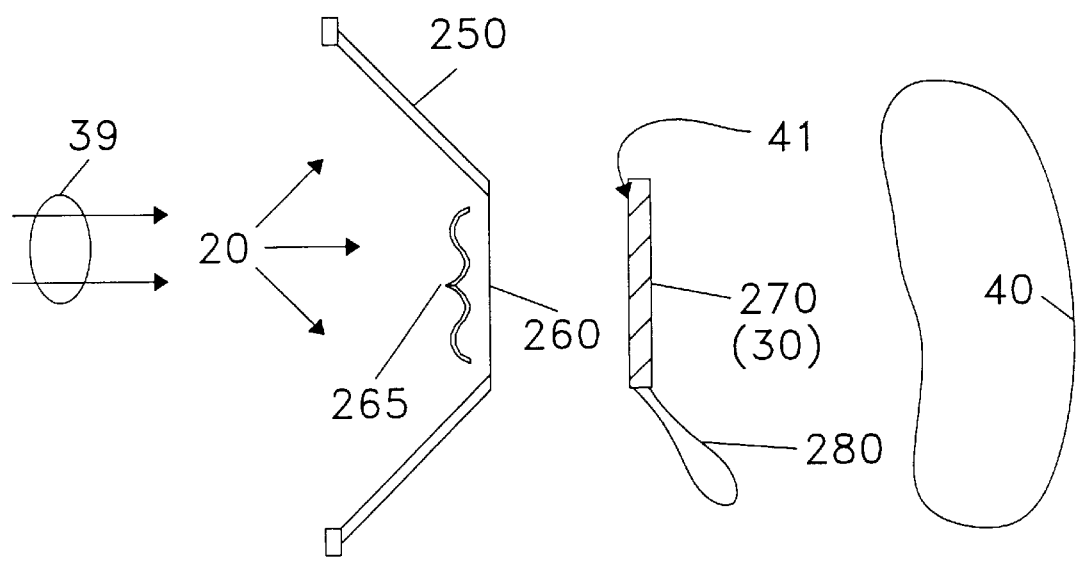
FIG. 2B shows the calibration device of FIG. 2A after a calibration target is removed (peeled) from a window of the device.

Once a measurement system is calibrated, the calibration target 270 is removed (peeled) from the window 260 by pulling on a tear tab 280, as shown in FIG. 2B. The system 3 is now ready to take measurements on a material or tissue 40 through the window 260 of the calibration device.

FIGS. 2C through 2E show an embodiment of the calibration device that includes an index matching agent. As shown in these figures, the calibration device includes a structure 250, a calibration target 270 having a calibration surface 41 and an index matching agent 293 contained within the structure 250 and covered with a seal 290. The index matching agent 293 could be a liquid or a gel that aids the instrument in taking an accurate measurement.

To use a calibration device that includes an index matching agent, one would first remove the seal 290 using a user graspable tab 295. The calibration device, without the seal 290, is shown in FIG. 2D. The calibration device would then be attached to a housing 298 of a measurement instrument, as shown in FIG. 2E. The housing may include a window 294 designed to abut the index matching agent 293 when the structure of the calibration device is mounted on the instrument. A bundle of optical fibers 299, that transmit and receive radiation, may abut the other side of the window 294.

Once the structure 250 of the calibration device is mounted on the housing 298 of the measurement instrument, a calibration measurement would be performed while the calibration target 270 is still attached to the structure 250. After the measurement instrument has been calibrated, the calibration target 270 would be removed from the structure 250 so that measurements can be performed on a material or tissue. All or a portion of the structure 250 may be made of a flexible material so that the structure 250 can flex when the instrument is pressed against the skin of a patient. This would cause the index matching agent 293 to completely fill the void between the patient's skin and the window 294 of the measurement instrument.

Figure 2G:
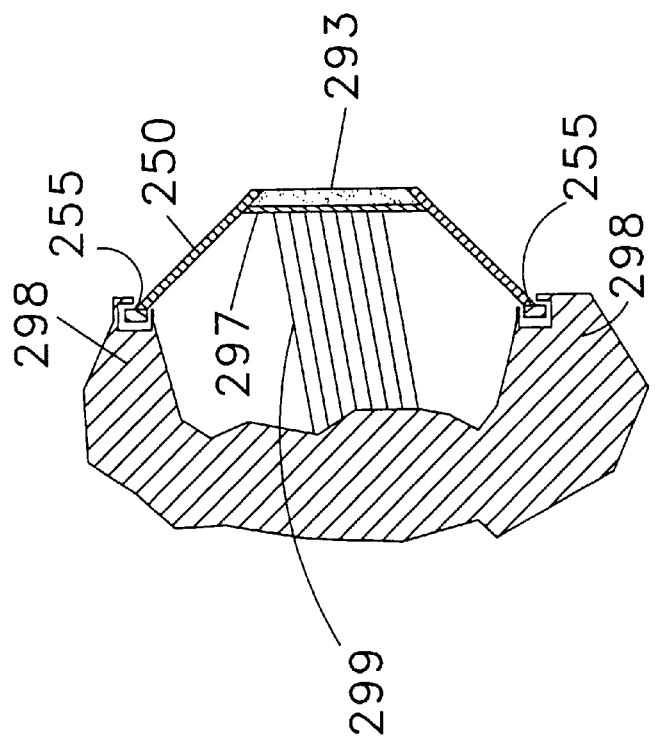
FIG. 2G shows the calibration device of FIG. 2F mounted on a measurement instrument wherein a removable calibration target has been peeled away from the device.
Figure 2F:
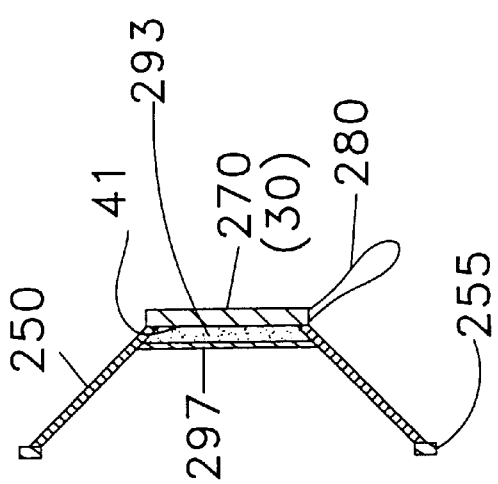
FIG. 2F is a schematic sectional representation of yet another embodiment of the calibration device for use with the measurement instrument.

Another calibration device embodying the invention is shown in FIGS. 2F and 2G. In this embodiment, the calibration device includes a structure 250 and a window 297. A calibration target 270 is attached to the structure 250 and an index matching agent 293 is trapped between the window 297 and the calibration target 270.

The calibration target would be mounted on a housing 298 of a measuring instrument, as shown in FIG. 2G. A bundle of optical fibers 299 can then abut a first side of the window 297 opposite the index matching agent 293. Once the calibration device is attached to the measurement instrument, a calibration measurement can be performed while the calibration target 270 is still attached to the structure 250. After calibration has occurred, the calibration target 270 could be removed so that measurements can be performed on a material or tissue.

Figure 3A:
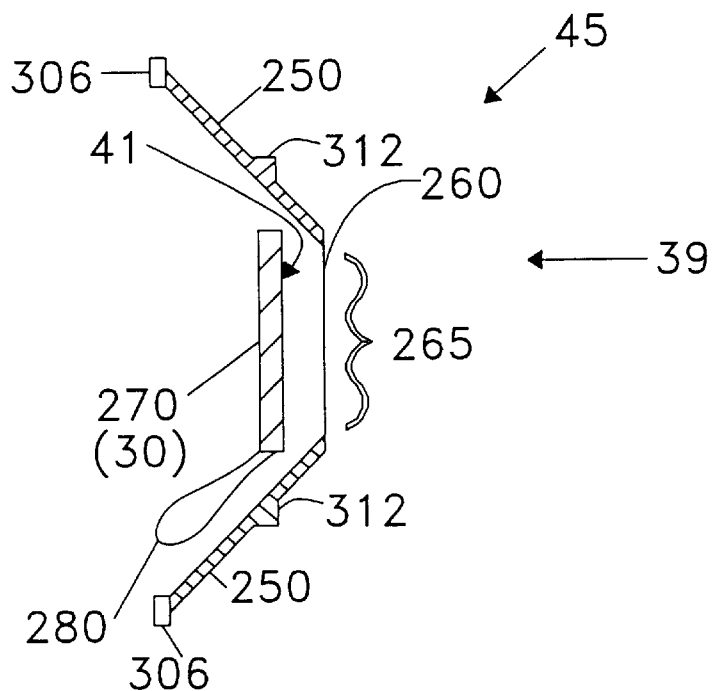
FIG. 3A is a schematic representation of yet another embodiment of a calibration device for use with a measurement instrument.
Figure 3B:
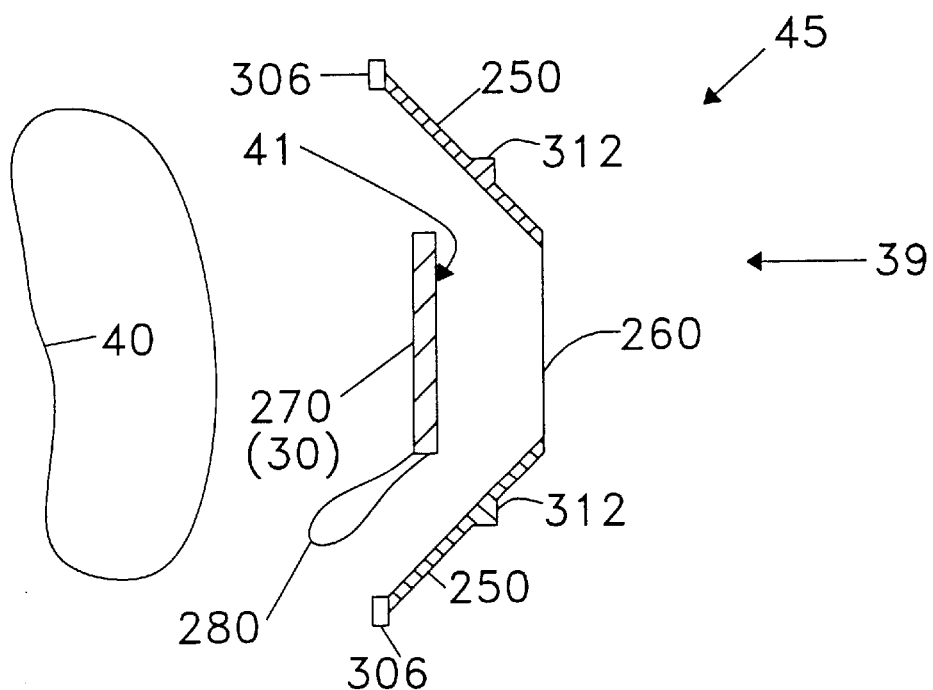
FIG. 3B is a schematic representation of the calibration device of FIG. 3A positioned adjacent a material or tissue to be measured with a calibration target partially removed from the device.

FIGS. 3A and 3B correspond to FIGS. 2A and 2B, but with radiation 39 entering from the right hand side, and the calibration target 270 attached to the window 260 within structure 250. In this case, an outer annular ring 306 comes into contact with a tissue or material 40 to be measured. Structure 250 also includes an annular ring or ridge 312, which is intended to be used to secure the device 45 to an instrument 10 (not shown).

Figure 3C:
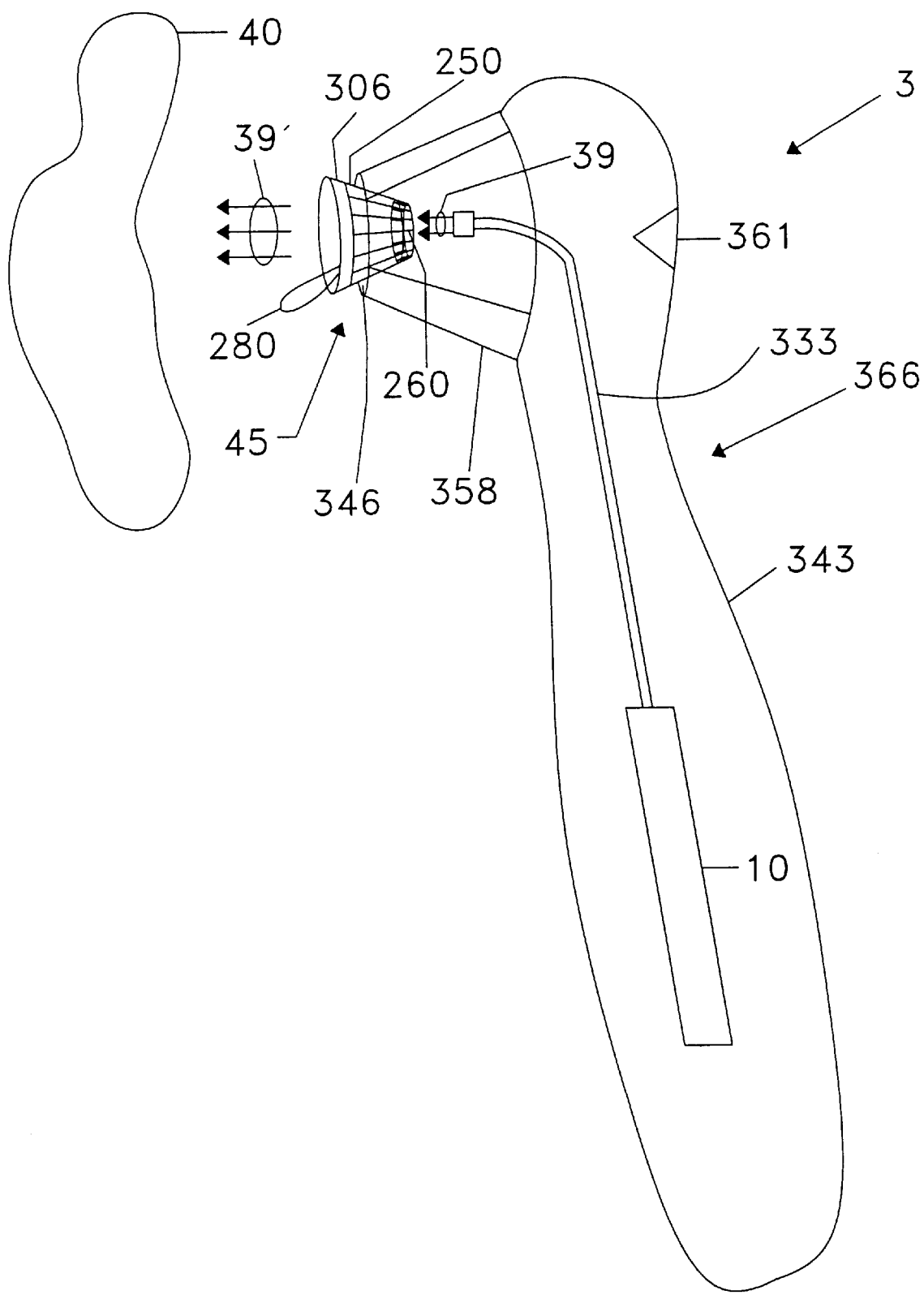
FIG. 3C shows a measurement system which utilizes a disposable calibration device as shown in FIGS. 3A and 3B.

FIG. 3C shows a measurement system 3 which utilizes a disposable calibration device 45. Here, the measurement instrument 10 is an optical instrument, such as a spectrometer, and radiation 39 is electromagnetic radiation which can be in the visible, UV and/or infrared regions. The system 3 includes a housing 343 which is easily graspable by a human hand. The instrument 10 is coupled to calibration device 45 via optical fibers 333. The calibration device 45 is inserted into an opening end 346 of a cone-shaped holder 358 of the housing 343. The cone shaped holder 358 can have any shape depending, among other things, on the shape of the calibration device 270. Hence, the holder 358 will alternatively be referred to as a calibration device receiving element. The holder 358 can be a separate piece, or part of the housing 343. It is preferable that the holder 358 be capable of receiving the calibration device 45 and allowing the calibration target 270 to be readily removed for the calibration device so that a measurement may be performed on a material or tissue 40. The holder 358 should also allow the calibration device 45 to be easily removed so that the system 3 is again ready to receive a new calibration device 45.

A curved portion 366 of the housing 343 allows the user's hand to comfortably hold the system 3. A user can initiate a calibration or measurement, as the case may be, by pressing a push button 361 with his or her thumb. Once a calibration measurement has been performed, a tear tab 280 is used to peel the calibration target 270 away from the window 260 (not shown in this view), and the system 3 is ready to make a measurement on a material or tissue 40.

Figure 3D:
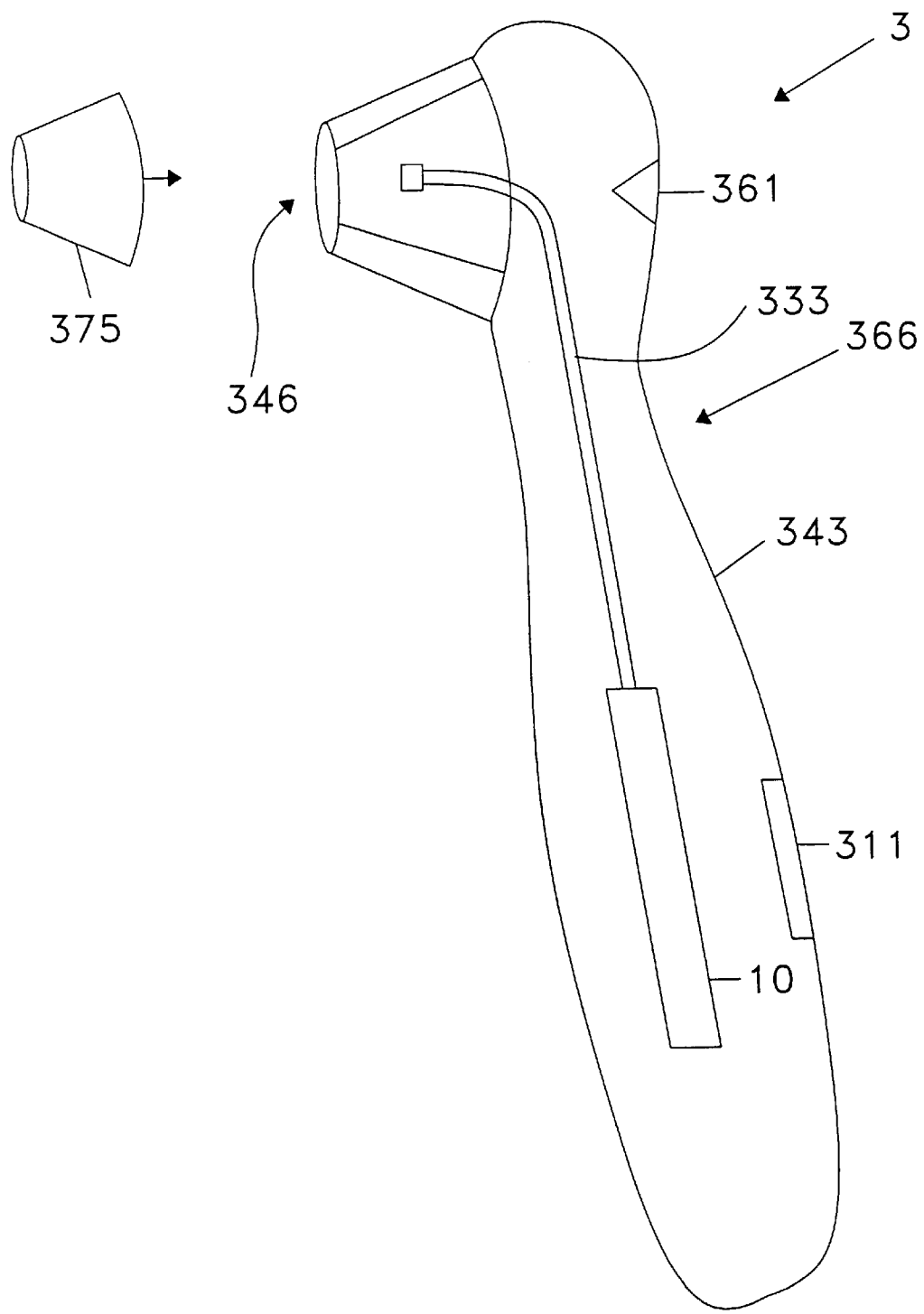
FIG. 3D shows the measurement system of FIG. 3C with the calibration device removed.

FIG. 3D shows the same measurement system with the calibration device 45 removed. A new calibration device 45 must be inserted into the holding end 346 of the system 3, the above discussed process of calibration repeated, and the calibration target 270 peeled away, before the measurement system 3 is ready to perform a new measurement. Alternatively, a cap 375 can be placed over the holding end 346 between measurements.

In all of the above embodiments, the calibration target 270 can have calibration information fitted directly on the surface 41 of the calibration target 270. This calibration information can include a message read by the instrument 10 which initiates a system shut down after one or a predetermined number measurements are performed. In the case of shut down upon a single measurement, contamination is avoided because the system 3 cannot be reused on a new or different material or tissue until a new calibration device 45 replaces the used calibration device. In an alternative approach, this calibration information can be directly input into system 3 by a user, using an input interface 311.

Figure 3E:
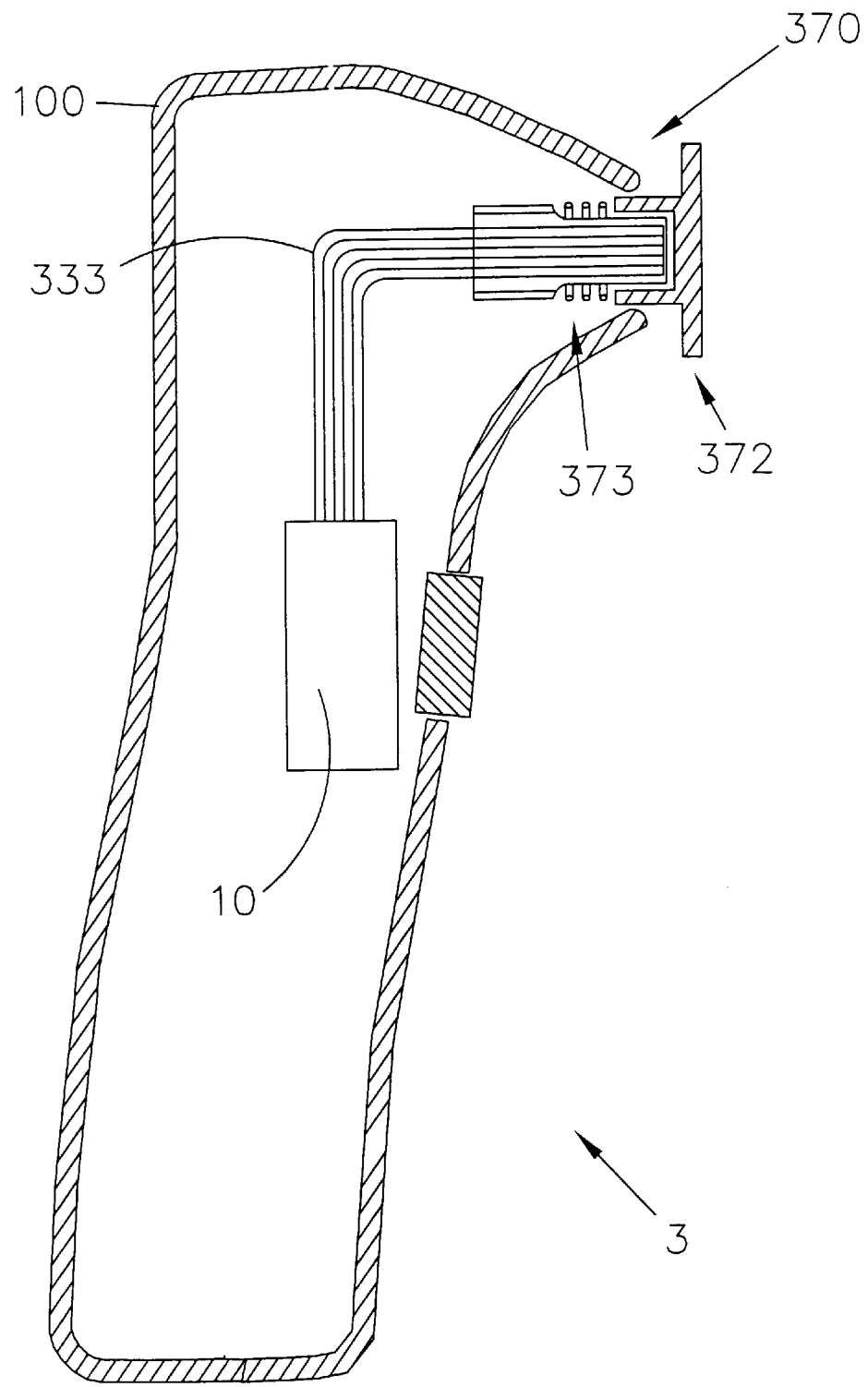
FIG. 3E is a cross-sectional view of a measurement system embodying the invention that includes a spring loaded annulus at a distal end of the measurement instrument.

FIG. 3E shows a cross-sectional view of a measurement instrument embodying the invention. The instrument includes a measurement device 10 coupled to an output end 370 of the system 3. An annulus 372, that surrounds a bundle of optical fibers 333, is mounted on the output end 370 of the system 3. The annulus 372 is mounted on the system 3 utilizing a spring 373, which biases the annulus 372 outward away from the measurement system 3. The annulus 372 may also be connected to a device that senses the position of the annulus 372 relative to the housing of the system 3.

According to one embodiment of the invention, the measurement device functions independently of spring 373 in that a measurement can be made regardless of whether or not spring 373 is biased.

According to another embodiment of the invention, when a user performs a measurement using the measurement system 3, the user would push the instrument against the skin of a patient so that the annulus 372 moves inward, against the bias of the spring 373. The movement would be sensed by a proximity sensing device. The proximity sensing device could then be used to output a signal when the annulus 372 is pushed far enough into the measurement system 3 such that a measurement can be performed by the measurement system 3. In a measurement system including a spring biased annulus 373, the proximity sensing device could be used to disable the device when the annulus 373 is too far out, and to enable the device to take a measurement when the annulus 372 is pushed a sufficient distance into the device such that a measurement can be accurately performed. The proximity sensing device could be a simple switch having electrical contacts, or a light emitter and corresponding sensor. Alternatively, the proximity sensor could directly sense the proximity of an output end of the measurement instrument to the patient's skin using an optical system or some other equivalent sensor, as would be well known in the art.

Figure 3F:
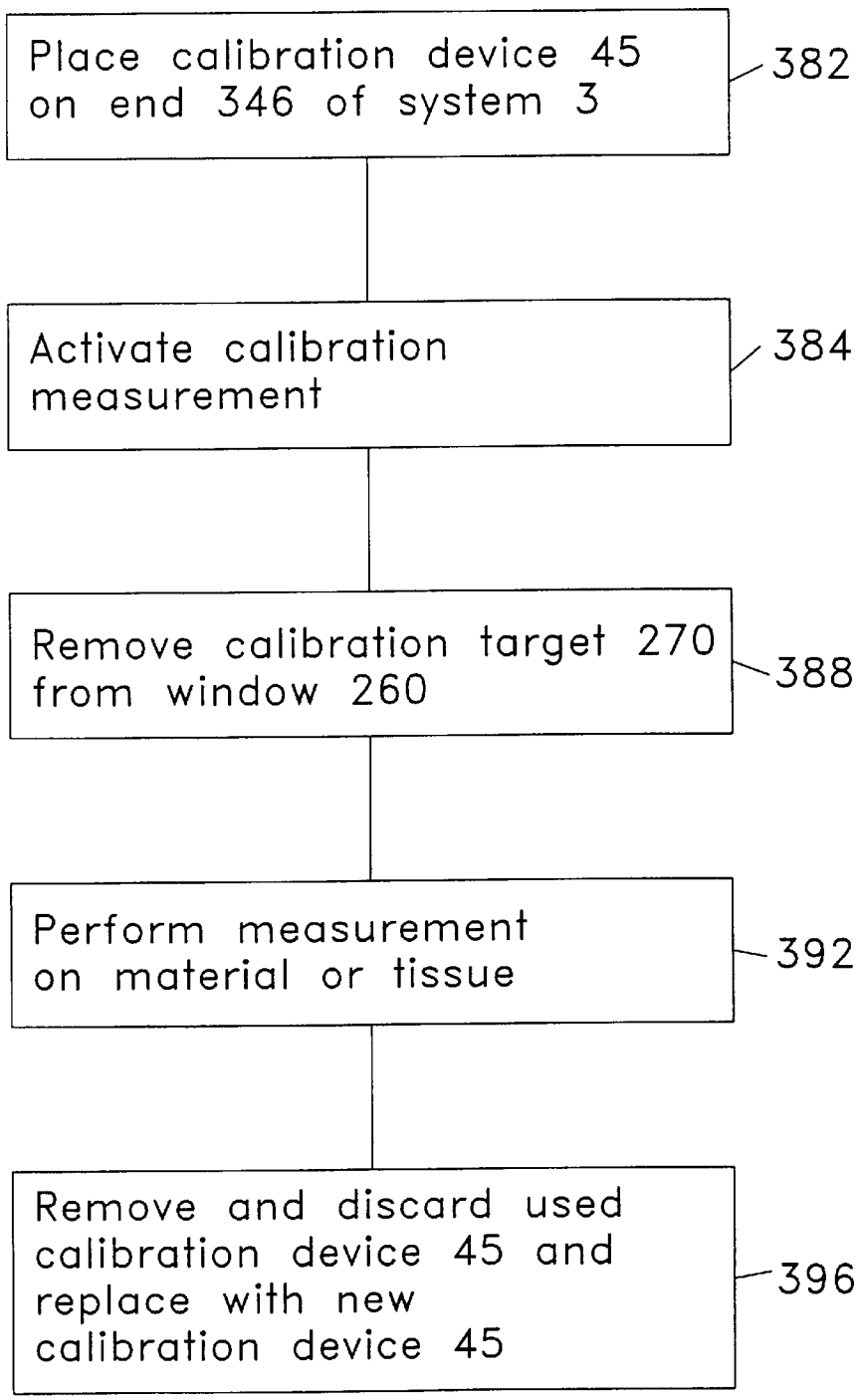
FIG. 3F is a flow chart summarizing the steps involved in calibrating a measurement instrument and taking a measurement on a material or tissue.

FIG. 3F summarizes the steps involved for the system 3 to take a measurement on a material or tissue 40. In particular, step 382 involves placing a calibration device 45 on the end 346 of the system 3. At this point, the calibration 45 device still has a calibration target 270 covering the window 260. A calibration measurement is performed by the system 3 at step 384 by pressing a push button 361, which activates the measurement instrument 10. Step 388 involves removing the calibration target 270 from the window 260 using the tear tab 280. Step 392 then involves performing a measurement on a tissue or material 40 to be measured. This might involve a single measurement or multiple measurements (if cross contamination is not an issue) on the same or a similar tissue or material. That is, if measurements are being performed on a person's skin, several measurements might be repeated in one vicinity, or at different locations on that person's body. Similarly, if measurements are being made on some type of material, multiple measurements can be made in one vicinity, or at multiple locations, provided that cross contamination is not an issue. Finally, once the measurement or measurements have been completed, the calibration device 45 is removed, discarded, and replaced with a new calibration device 45 at step 396. Alternatively, a used calibration device 45 can be removed, discarded, and a cap 375 can be placed over the end 346 until a new measurement is to be made.

Figure 4A:
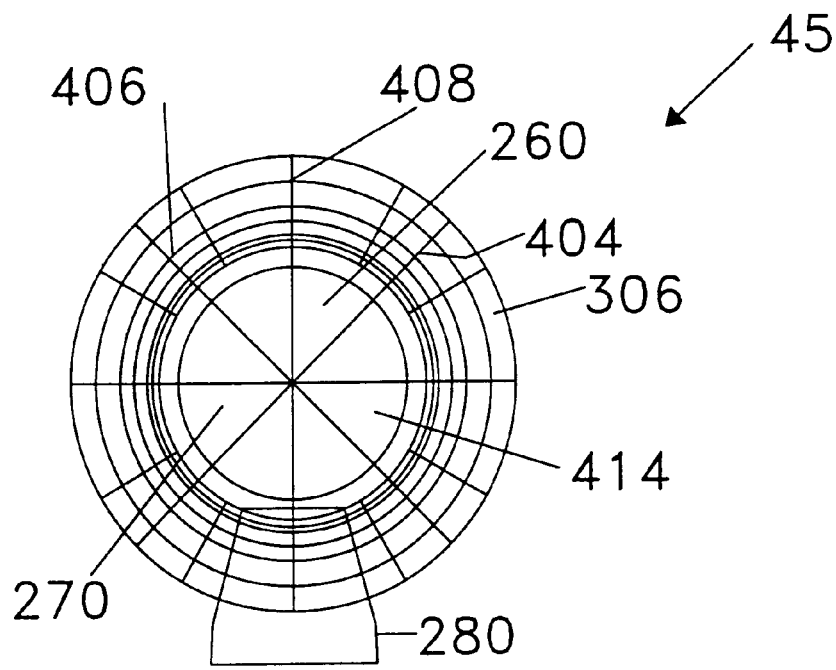
FIG. 4A is a top view of a calibration device embodying the invention.
Figure 4B:
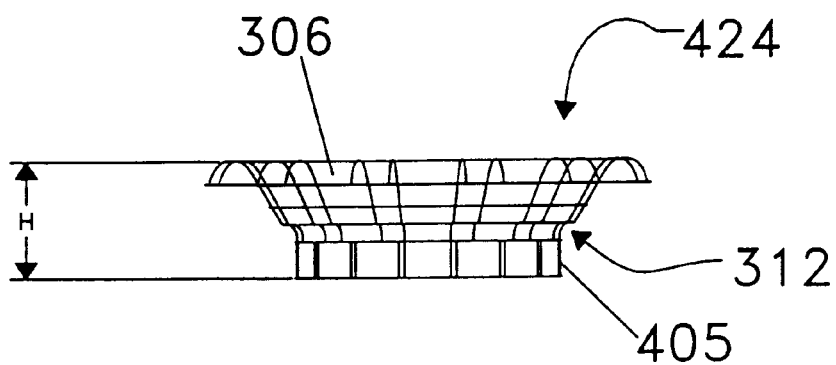
FIG. 4B is a side view of the calibration device of FIG. 4A.
Figure 4C:
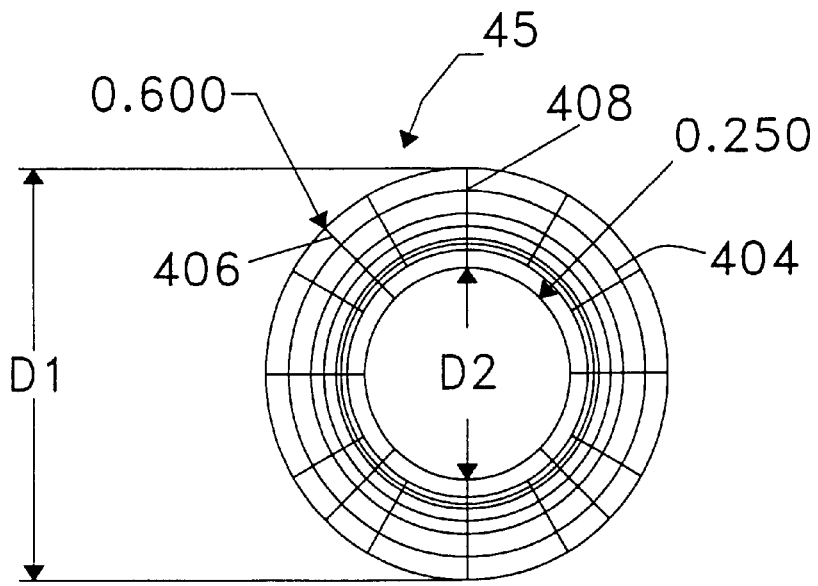
FIG. 4C is a plan view of the calibration device of FIG. 4A with a calibration target removed.
Figure 4D:
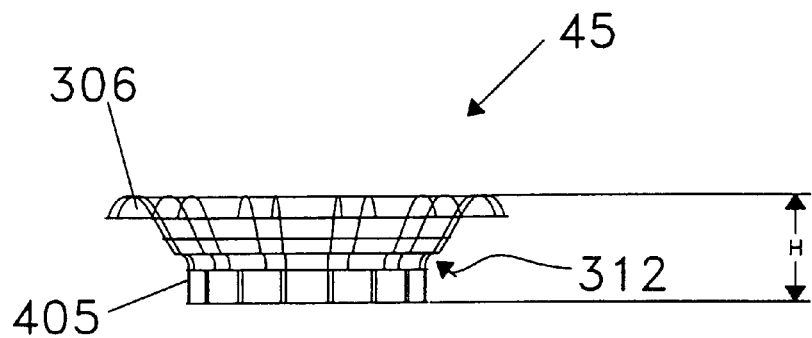
FIG. 4D is a side view of the calibration device of FIG. 4B with a calibration target removed.

FIGS. 4A and 4B show a plan view and a side view, respectively, of a calibration device 45 similar, but not identical, to the calibration device 45 shown in FIGS. 3A and 3B. FIGS. 4C and 4D show the same views as FIGS. 4A and 4B, respectively, with the calibration target 270 removed. The calibration device 45 can include cross-hatched lines 404, 406, and 408. Lines 404, 406, and 408 can be placed on the backside 414 of the calibration target 270, as well as along inner-sides 424 of the structure 250 and the outer annular ring 306 of the calibration target 270, which can aid in the placement of the window 260 on a material or tissue 40 to be measured. The cross-hatched lines 404, 406, and 408 are designed to be aligned prior to calibration. Once the calibration measurement is made, the calibration target 270 is removed, thereby making the system 3 ready to take a calibrated measurement. If a user then tries to re-attach the calibration target 270, they will note that the lines 404, 406 and 408 are no longer properly aligned. Also, the surface 41 of the calibration target 270 can be made so that once a calibration measurement is made, the calibration target 270 no longer attaches or sticks to the window 260. The cross-hatched lines 404, 406 and 408 define six zones (here each zone is shown as a wedge, but the shape can be of any form). Also, note that an additional cross-hatched line is shown which further divides two of the wedges, and hence the number of zones need not be limited to six. Each of the cross-hatched lines are made to appear on both the calibration target 270 and the window 260. The different zones on the calibration target 270 may have different reflectivities or different reflectance signatures. The different zones on the calibration target 270 are matched up with corresponding zones on the window 260 at the manufacturing stage. The different zones on the calibration target 270 thereby create a rotary reflectance signature. In this manner, calibration is only valid if the rotary reflectance signature is duplicated with each calibration measurement. If the calibration target 270 is not properly oriented, the calibration would not be valid. This helps to avoid the reuse of a calibration device 45 or a calibration target 270.

Figure 4E:
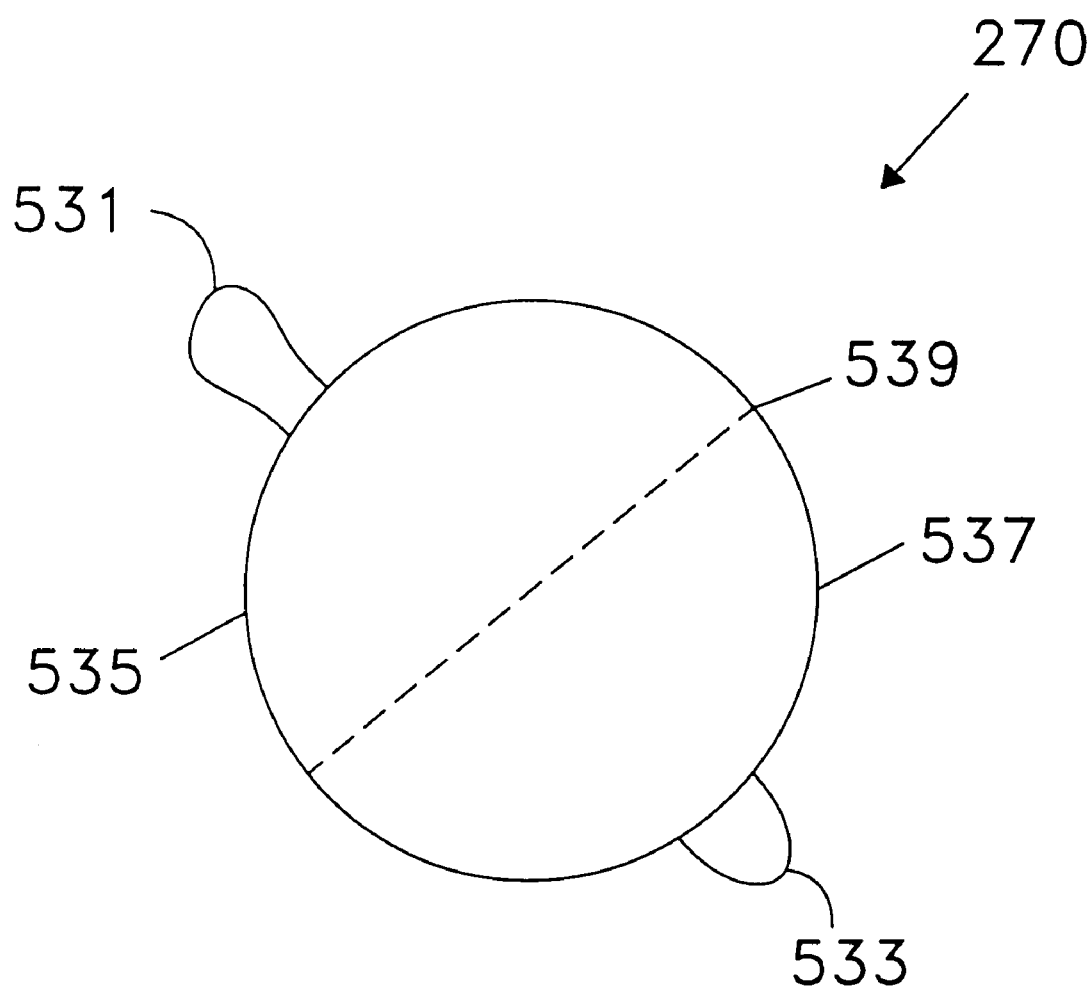
FIG. 4E is a plan view of a calibration target with two pull tabs and a perforation down the middle designed to prevent reuse.

The calibration target 270 can be manufactured with two pull tabs at its sides, as shown in FIG. 4E. Here, two pull tabs 531 and 533 are attached to two halves 535 and 537 of the calibration target 270. Between the two halves 535 and 537 is a mechanical perforation 539. When the calibration target 270 is pulled away from the window 260 (see FIGS. 2A or 2B) by one of the tabs, it breaks along perforation 539, thereby making it difficult to reuse. The remaining half of the calibration target 270 can then be pulled away using the remaining tab. The perforation 539 need not be a straight line, but can be curved or spiral shaped. If the perforation 539 is a spiral, a single tab (e.g., tab 531) can be used, in which case the calibration target 270 is unraveled and peeled away from window 260 either from its perimeter to its center (if the tab is on the perimeter of the target 270), or from its center to its perimeter (if the tab is on the center of the target 270). The number of revolutions of the perforation spiral can vary from less than one to three or more.

The calibration device 45 shown in FIGS. 4B and 4D has an annular ring 301 which contacts the material or tissue 40 to be measured. Device 45 also has a collar section 405 that attaches to an optical outlet (not shown) of the measuring instrument 10. Diameter D1 is defined to be the diameter of the annular ring 306 and diameter D2 is defined to be the diameter of the window 260. Height H is defined to be the distance from the window 260 to the annular ring 306.

Figure 5A:
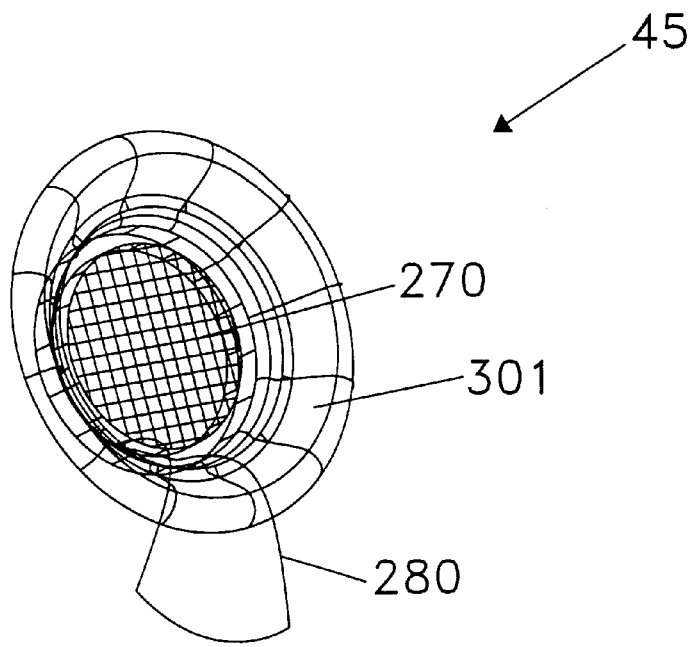
FIG. 5A is a perspective view of the calibration device of FIG. 4A.
Figure 5B:
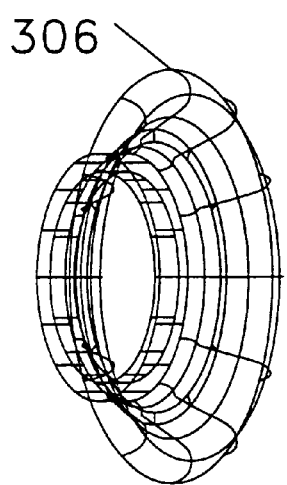
FIGS. 5B, and 5C are perspective views of the calibration device of FIG. 4A with the calibration target removed.
Figure 5C:
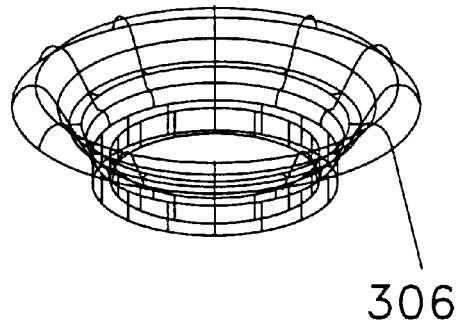

FIGS. 5A, 5B, and 5C show three perspective views of the calibration device 45 of FIGS. 4A–4D. In FIGS. 5B and 5C, the calibration target 270 is removed.

Figure 6:
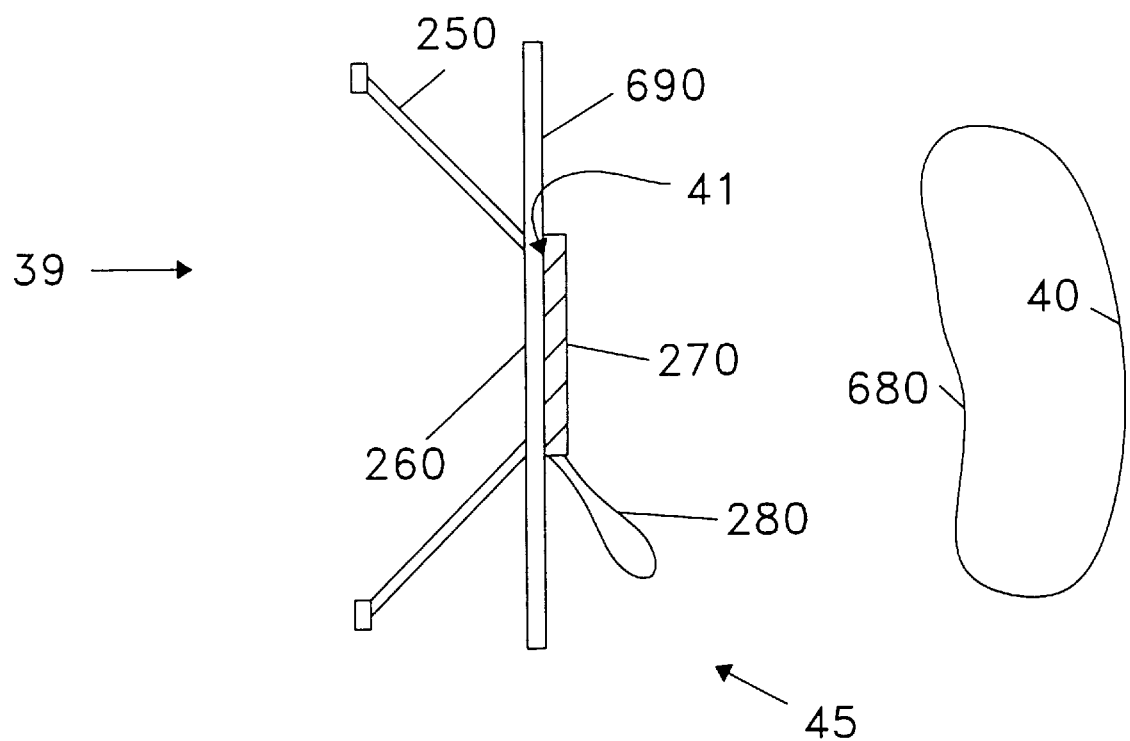
FIG. 6 is a schematic representation of another calibration device embodying the invention.

FIG. 6 shows a calibration device 45 according to another embodiment of the invention. Here, a landing annulus 690 is affixed to the structure 250. The landing annulus 690 serves to fix the angle at which radiation is incident on the surface 680 of a material or tissue 40 being measured. The landing annulus 690 is preferably transparent to radiation 39. Calibration occurs, as before, using the calibration target 270. The calibration target 270 is then removed, and the annulus 690 remains in place. The measuring instrument, with the attached calibration device 45, is then placed on the surface 680, such that the annulus 690 lies flat on the surface 680. This ensures that radiation 39 is incident approximately normal to the surface 680, as it was to the surface 41 of the calibration target 270. On the other hand, depending on the type of measurement, it may be preferable, due to unwanted spectral reflections, to have radiation 39 incident at an angle relative to an axis normal to the surface 680. The landing annulus 690 can be a separate piece affixed to the structure 250 and comprised of any type of rigid material such as various plastics. If infection to the surface 680 of tissue 40 is an issue, then the landing annulus 690 should be removable from the structure 250. Alternatively, annulus 690 can simply be an extension of window 260 itself.

The structure 250 is preferably fabricated from molded plastic with a smooth window zone defined for the window 260. Using plastic molding allows the structure 250 to be fabricated at low cost and in a wide variety of shapes and sizes. The calibration target 270 can also be fabricated from plastic and may also have a dye or other material added to the surface 41 to provide sufficient spectral detail to effect the necessary calibration. The calibration target 270 can be attached to the window section 260 in such a way that once removed, it cannot be readily re-attached. One implementation is to fabricate the calibration target 270 using a statically clinging type plastic, and to fabricate structure 250 using an appropriate material such as an acrylic called polymethyl methacrylate (PMMA), both of which are available from 3M Corporation.

Figure 7A:
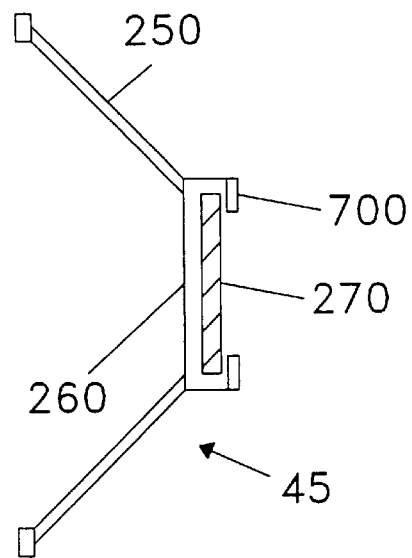
FIG. 7A is a schematic side view of another calibration device embodying the invention.
Figure 7B:
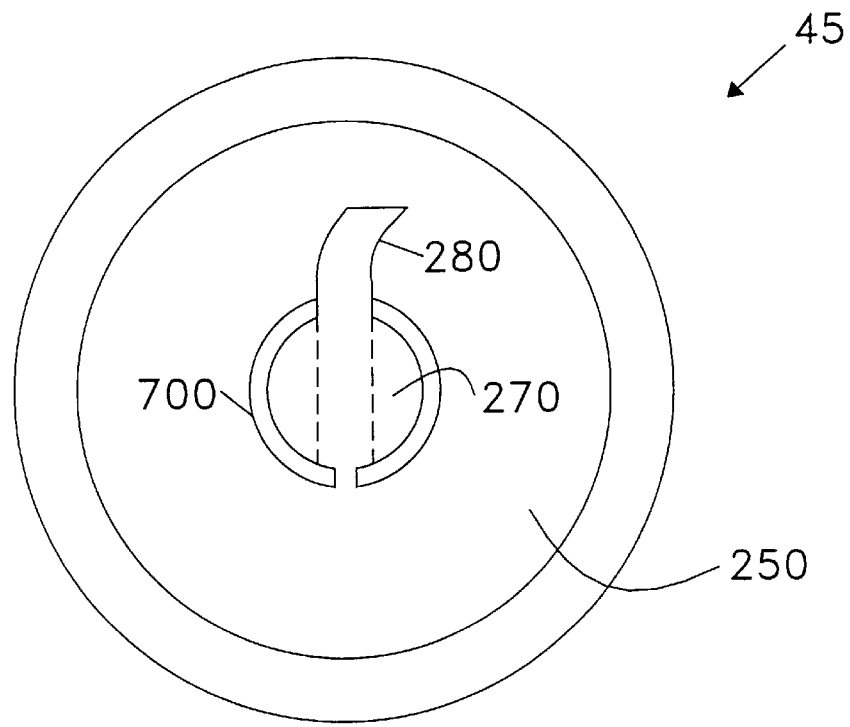
FIG. 7B is a plan view of the calibration device of FIG. 7A.

FIG. 7A shows a side view of a calibration device 45 according to yet another embodiment of the invention. Here, the calibration target 270 is held in place by a ridge 700 alone, or together with static cling between the calibration target 270 and the window 260. The ridge 700 can be part of the window 260, or a separate piece. FIG. 7B shows the calibration device 45 as viewed from above.

Figure 8A:
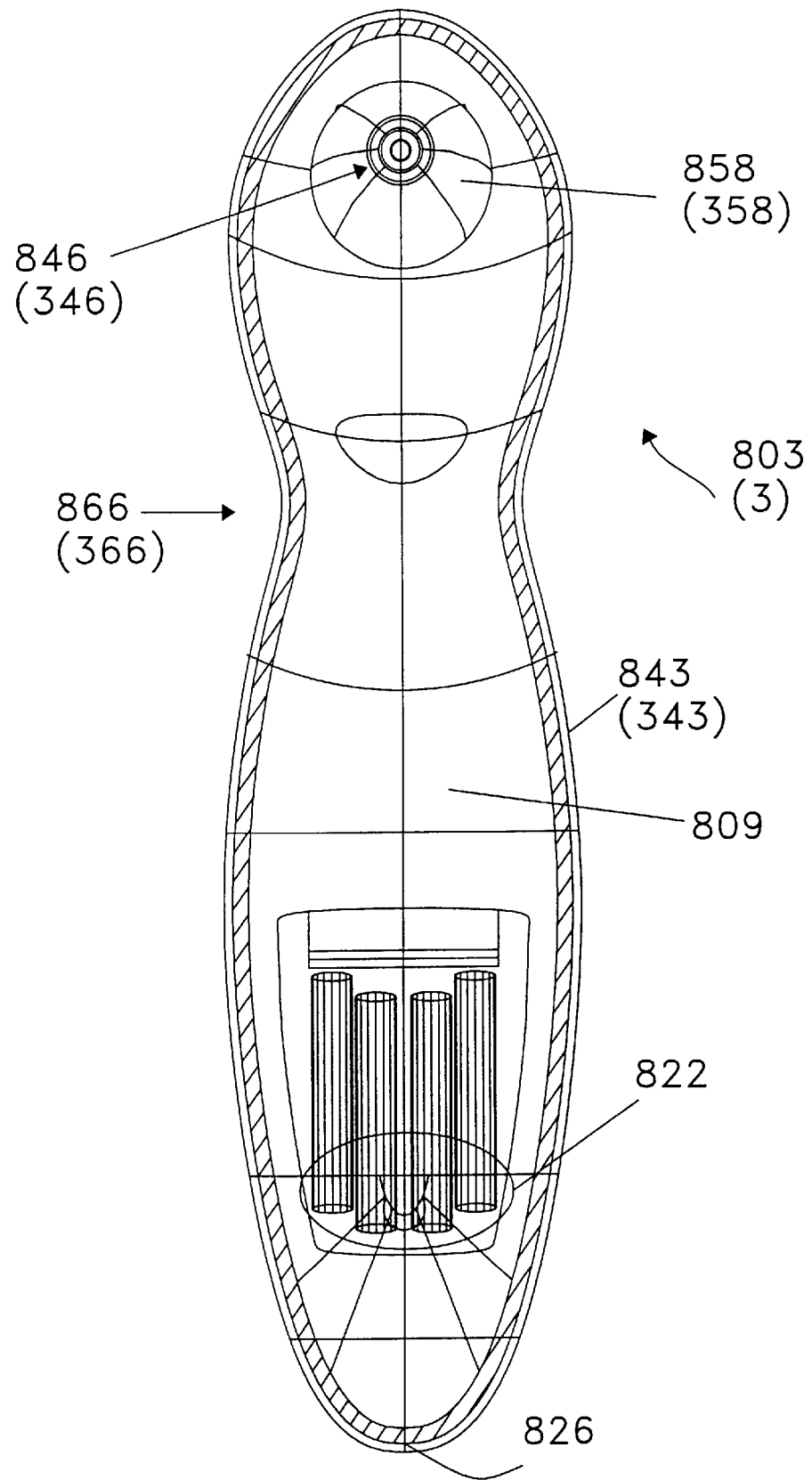
FIGS. 8A, 8B, and 8C show front, side and back views, respectively, of a measurement instrument embodying the invention.
Figure 8B:
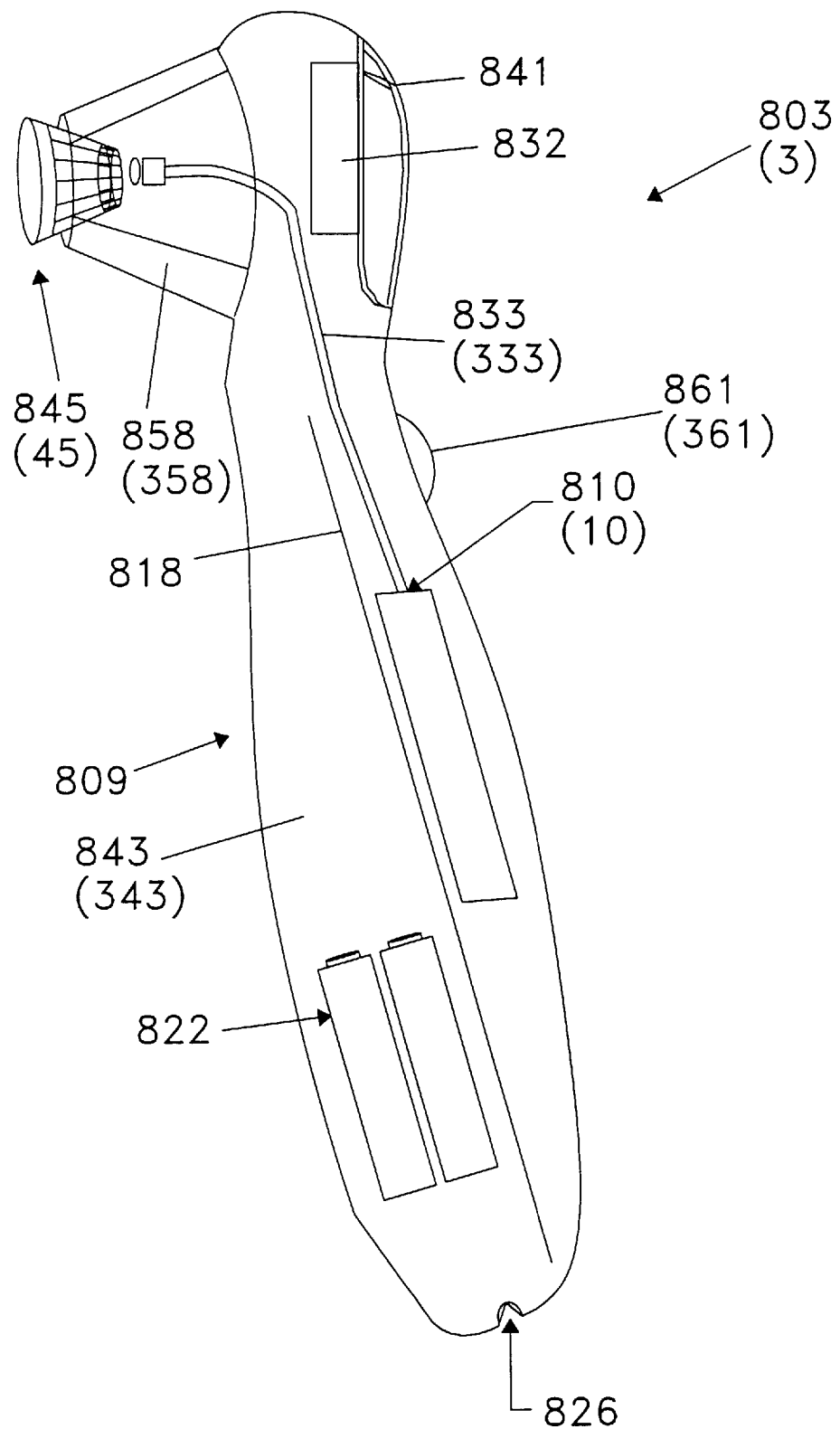
Figure 8C:
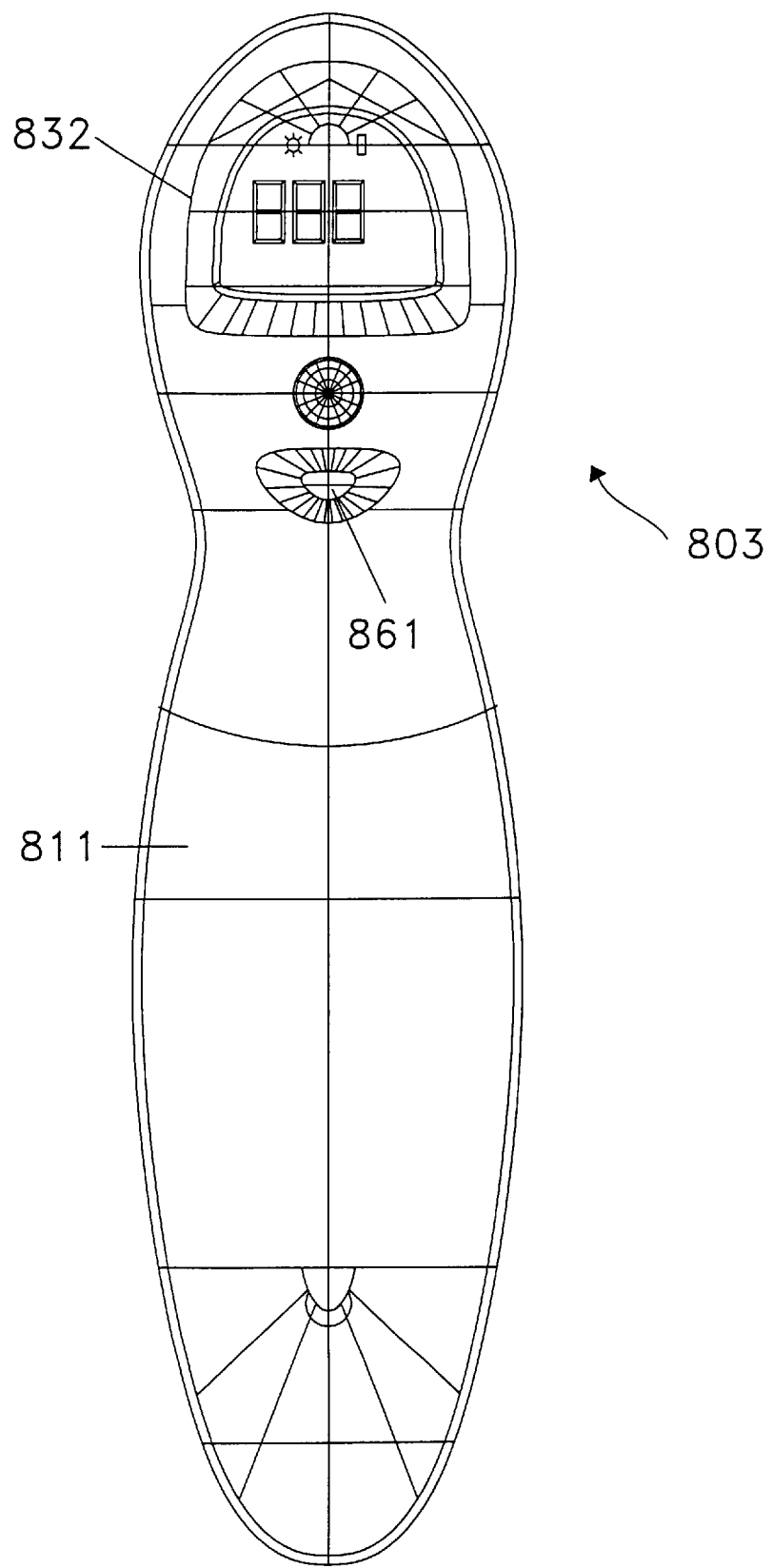
Figure 8D:
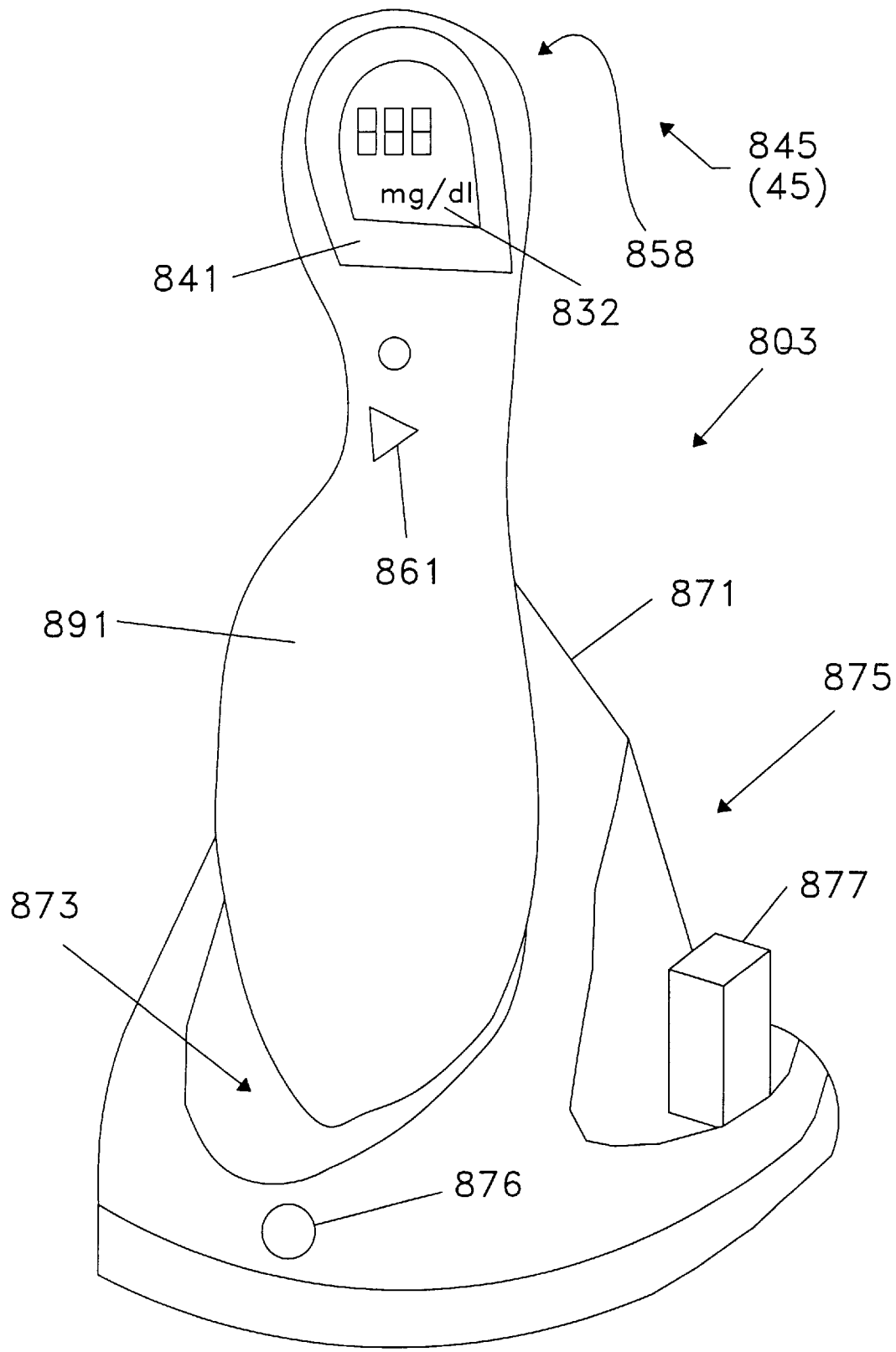
FIG. 8D shows a measurement instrument embodying the invention in a charging stand.

FIGS. 8A, 8B, and 8C show front, side and back views, respectively, of a measurement system 803 embodying the invention. FIG. 8D shows the measurement system 803 in a charging stand 871. The elements in the measurement system 803 which have similar counterparts in the previously discussed system 3, will also have the earlier reference numbers indicated in parenthesis.

As will be discussed with reference to FIG. 9, the radiation analyzer 810 can include a microspectrometer such as that offered by American Laubscher Corporation of Farmingdale, N.Y. called the VIS/NIR microspectrometer. The measurement system 803 can operate in the visible, UV and/or infrared regions.

The measurement system 803 includes a housing 843 which is sized so as to be easily graspable by a human hand. A radiation analyzer 810 is coupled to the calibration device 845 via one or more optical fibers 833 (see FIG. 8B). The calibration device 845 is inserted into an opening end 846 of a cone-shaped holder 858 of the housing 843. A curved portion 866 of the housing 843 allows the user's hand to comfortably hold the measurement system 803.

FIG. 8B shows a side view of the measurement system 803, including the radiation analyzer 810 and a push button 861. The radiation analyzer 810 is mounted on a printed circuit board (PCB) 818, which is powered by batteries 822. The batteries 822 can be recharged when the system 803 is placed in a power adapter stand through a charger connection 826. A liquid crystal display (LCD) device 832 is also coupled to the PCB 818. An LCD device 832, which is visible through a window 841, displays measurement results, instructions, warnings, and other operating information. The radiation analyzer 810 is controlled by a processor (see FIGS. 9A and 9B) also mounted on PCB 818.

FIGS. 8C and 8D show a back view of system 803, which includes back portion 891 and the LCD device 832. A person can initiate a calibration, and then a measurement, by pressing push button 861 with his or her thumb. In particular, once a calibration measurement has been performed, the tear tab 280 (see previous figures) is used to peel the calibration target 270 away from the window 260, and the system 803 is ready to make a measurement on a patient. The LCD device 832 indicates when the measurement system 803 is ready to make a calibration measurement, when a calibration measurement has been completed and the system 803 is ready to make an actual measurement, and when the system 803 has completed a measurement. The LCD device 832 also displays the results of measurements, and messages or other indicators. For instance, the LCD device 832 might show that a particular calibration target 270 has already been used and that no additional measurements can be made until a new calibration measurement is made.

A limit switch (not shown) may be installed at the end of the tip 858 to detect the presence of a calibration device 45. Once the limit switch is engaged, a calibration measurement is enabled and a measurement counter is initialized to zero. Calibration is then performed to ready the device for taking measurement. The system software then increments the counter each time a measurement is made, up to a predetermined maximum. Once the maximum number of measurements is reached, the system software indicates that a calibration is again required, and the device is prevented from taking additional measurements. Should the limit switch be disengaged at any time in the measurement sequence, indicating the removal of the disposable tip, the display indicates that a new calibration sequence must be begun before other measurements may be taken. These software controls prevent an operator from using one calibration target more than a predetermined number of times before replacing the calibration device.

FIG. 8D shows a measurement system 803 with a charging stand 871 for storing and charging the system 803. The charging stand 871 includes a center portion 873 for receiving the system 803. The center portion 873 serves as both a stand and a recharging unit. The stand 871 has an electrical cord (not shown) which can be plugged into an outlet. The stand 871 also includes an electrical receiving unit which receives charger connection 826 (see FIG. 8B) of the system 803. An indicator light 876 indicates when the measurement system 803 is properly placed in the center portion 873 so that recharging may take place. The stand 871 further includes a side receiving portion 875 which can be used to hold a supply 877 of calibration devices 845.

Figure 9A:
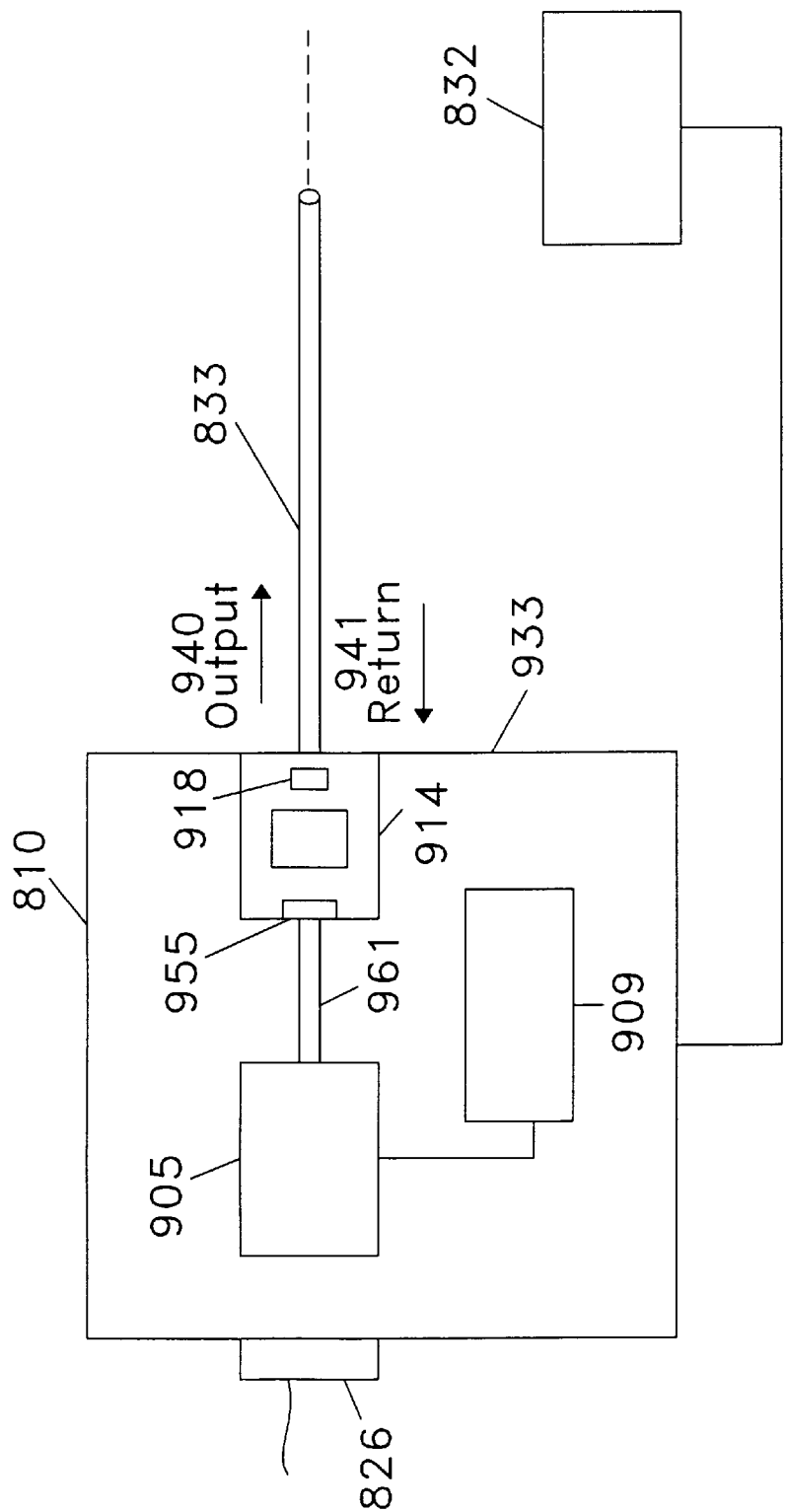
FIG. 9A is a schematic diagram of certain elements of a measuring instrument embodying the invention.
Figure 9B:
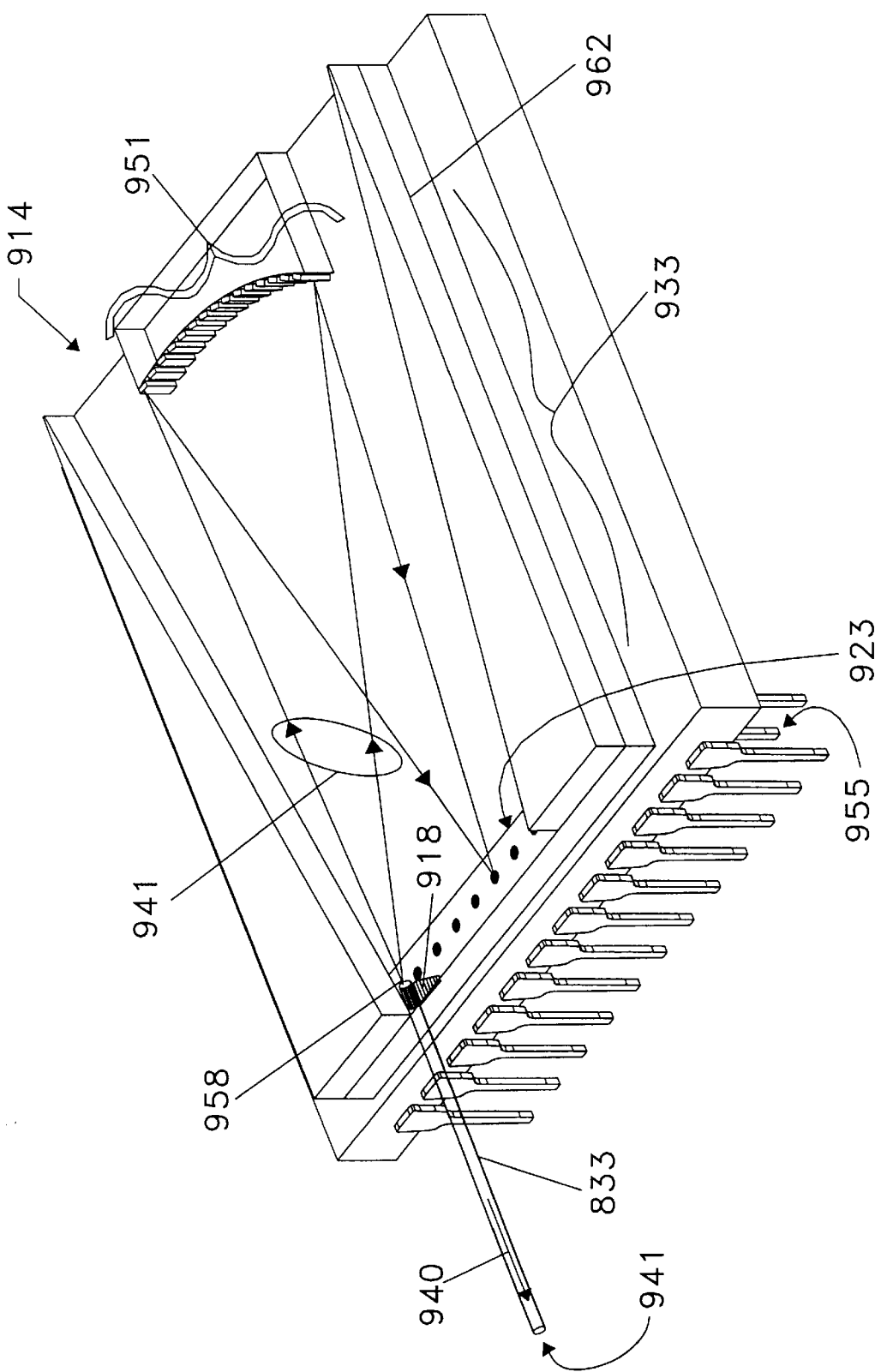
FIG. 9B shows a cut away view of an optical unit of the measurement instrument of FIG. 9A.

FIG. 9A is a schematic diagram of certain elements of a measurement system 803, and in particular, of a radiation analyzer instrument 810. The radiation analyzing instrument 810 includes an optical unit 914, a central processor unit (CPU) 905, and a memory 909. FIG. 9B shows a perspective view of an optical unit 914 that including an optical source 918, a detector array 923, an optical grating 951 and an output 955 which couples the optical unit 914 to the CPU 905 via a data bus 961. The optical source 918 may be a tungsten halogen bulb, a noble gas filled tungsten bulb or several LED's covering the desired regions of the optical spectrum. The optical source 918 may also be placed at a location in the device housing to illuminate the subject directly, without coupling the radiation into a fiber.

The embodiment shown in FIG. 9B utilizes a microspectrometer offered by American Laubscher Corporation of Farmingdale, LI, N.Y. called the VIS/NIR microspectrometer. Optical radiation 940 is output from optical source 918 and is transmitted via fiber 833 to the target (not shown) to be measured. The return signal 941 travels back down optical fiber 833 and is output from fiber end 958 into a type of waveguide 962 (cut away) and is incident on diffraction grating 951. Diffraction grating 951 achieves self-focussing of radiation 941 to different points or detectors on diode array 923, depending on the intensity and wavelengths of the return radiation 941.

The operation of system 803 will now be described in conjunction with FIGS. 9A and 9B. First, calibration target 270 starts out being arranged on window of device 45 and a user pushes a button 861, which indicates that a calibration measurement should be taken. Radiation 940 is emitted toward the calibration target 270, which reflects at least a portion of the radiation back to the measurement system. Because the calibration target 270 has a known spectral characteristic, the returned radiation 941 results in a detected intensity at individual detectors on the detector array 923, thereby yielding a measured calibration characteristic. This measured calibration characteristic is compared to the expected or known spectral characteristic of the calibration target 270, and a resulting adjustment value (which could be an array of values) is determined. Calibration target 270 is then removed, and a measurement of tissue or material 40 is made by outputting radiation 940 as above. A resulting spectral characteristic is then output from detector array 923, which in turn is adjusted by CPU 905 using the adjustment value or characteristic to yield a calibrated spectral characteristic. The calibrated spectral characteristic can then be used to determine some measurable characteristic of the material or tissue 40. One such measurement is a non-intrusive bilirubin measurement according to one embodiment of the invention, as will be discussed below.

Figure 12:
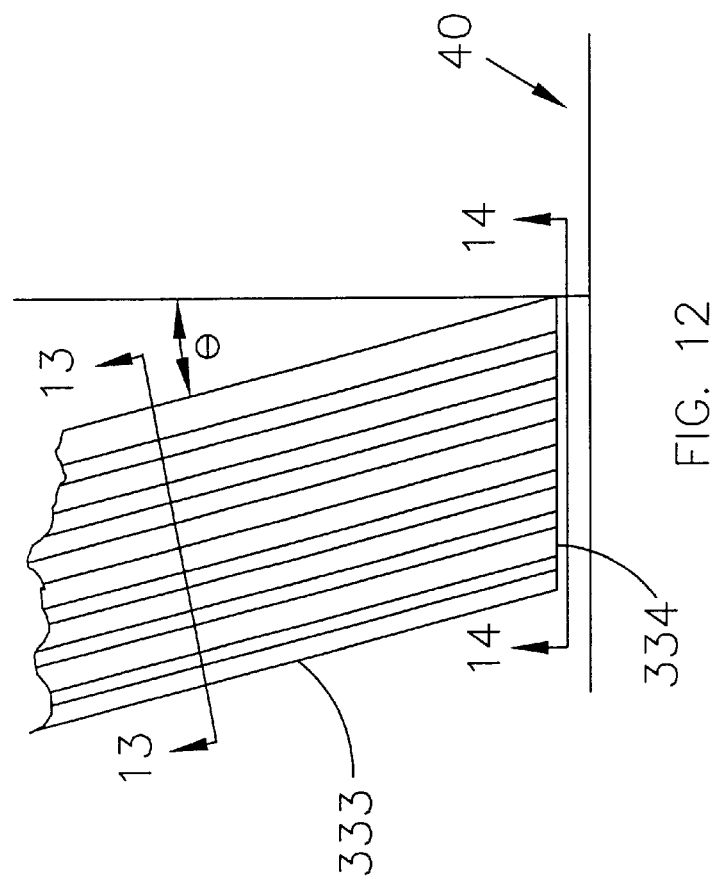
FIG. 12 is a diagram showing a fiber optic bundle of a measurement instrument embodying the invention adjacent a tissue or material being measured.

The optical fiber 833 of measurement device 803 may comprise one or a plurality of fibers. Preferably, the optical fiber 833 comprises a plurality of fibers arranged in a bundle. FIG. 12 shows a bundle of optical fibers 333 which can be used to transmit and receive radiation. The optical fibers are arranged so that they approach a surface of a material or tissue 40 to be measured at an angle θ relative to an axis perpendicular to the surface of the material or tissue 40. When the bundle of optical fibers is inclined in this manner, backscattering effects are reduced. Angle θ is preferably not 0° and sufficiently large to prevent backscattering effects. In one embodiment, angle θ is between a few degrees and 20° and preferably between 5° and 10° and more preferably approximately 7°.

Figure 13:
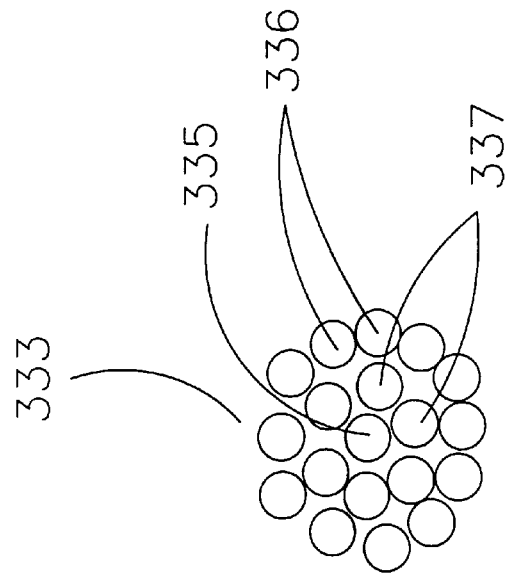
FIG. 13 is a sectional view of the fiber optic bundle of FIG. 12 as seen from section line 13—13.

FIG. 13 shows the bundle of optical fibers 333 as seen from section line 13—13 of FIG. 12. In the bundle of optical fibers 333, there is an outer ring of transmission optical fibers 336, an inner ring of transmission fibers 337 and a central receive optical fiber 335. When the device is in operation, radiation is transmitted through the first and second rings of transmission fibers 336, 337, is reflected off the skin of a patient, and received by the receive optical fiber 335.

Figure 14:
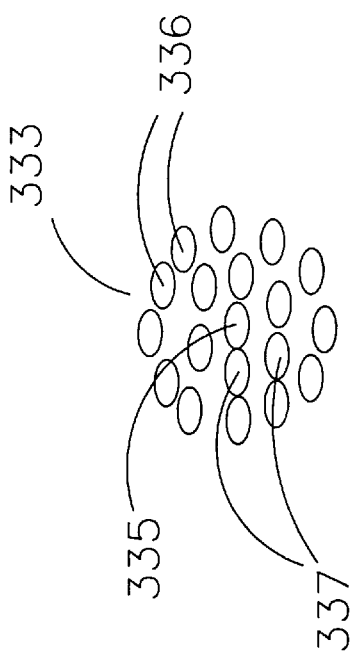
FIG. 14 is a sectional view of the fiber optic bundle of FIG. 12 as seen from section line 14—14.

FIG. 14 shows the bundle of optical fibers as seen from section line 14—14 of FIG. 12. Because the ends of the optical fibers are cut at a slight angle, and because the optical fibers themselves are cylindrical, the ends of the optical fibers appear to be ovals in FIG. 14.

Figure 17:
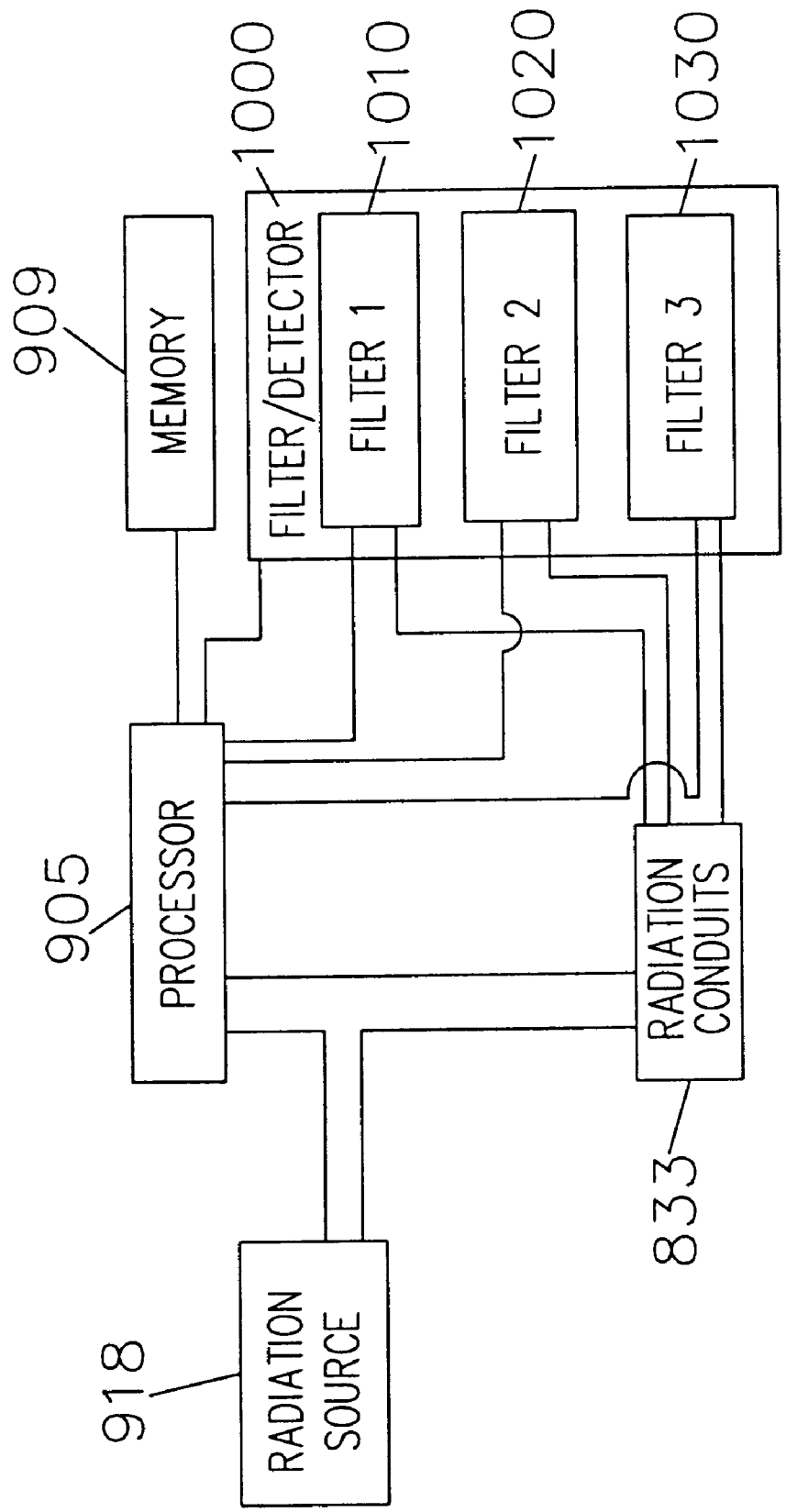
FIG. 17 is a block diagram of parts of a measurement instrument embodying the invention.

Although a microspectrometer as shown in FIG. 9B may be used in an embodiment of the invention, other devices capable of measuring the amplitude of radiation reflected from a patient's skin at different wavelengths can also be used. For instance, FIG. 17 shows a radiation analyzing device that includes a processor 905, a radiation source 918, radiation conduits 833, such as optical fibers, a memory 909 and a filter/detector unit 1000. The filter/detector unit may comprise a plurality of detectors and filters. For instance, filters 1, 2 and 3 1010, 1020 and 1030, may be designed to pass only discreet wavelengths of the radiation reflected from a patient's skin. Each of the filters may be paired with a corresponding detector to determine the amplitude of light reflected from a patient's skin at each of the three filter wavelengths. Alternatively, the filters may be successively coupled to a single detector to determine the amplitude of the reflected light at each of the filter wavelengths. In yet another embodiment, the filter/detector unit 1000 may comprise a detector with a linear variable filter.

If the radiation conduits 833 of the device shown in FIG. 17 comprise optical fibers, the numerical aperture of the optical fibers can be selected to optimize the efficiency of the device. For instance, the optical fibers used to transmit radiation from the radiation source 918 to the patient's skin may have a numerical aperture matched to the radiation source 918. In addition, the optical fibers used to transmit light reflected from the patient's skin to the radiation analyzer may have a numerical aperture matched to the radiation analyzer.

Figure 15:
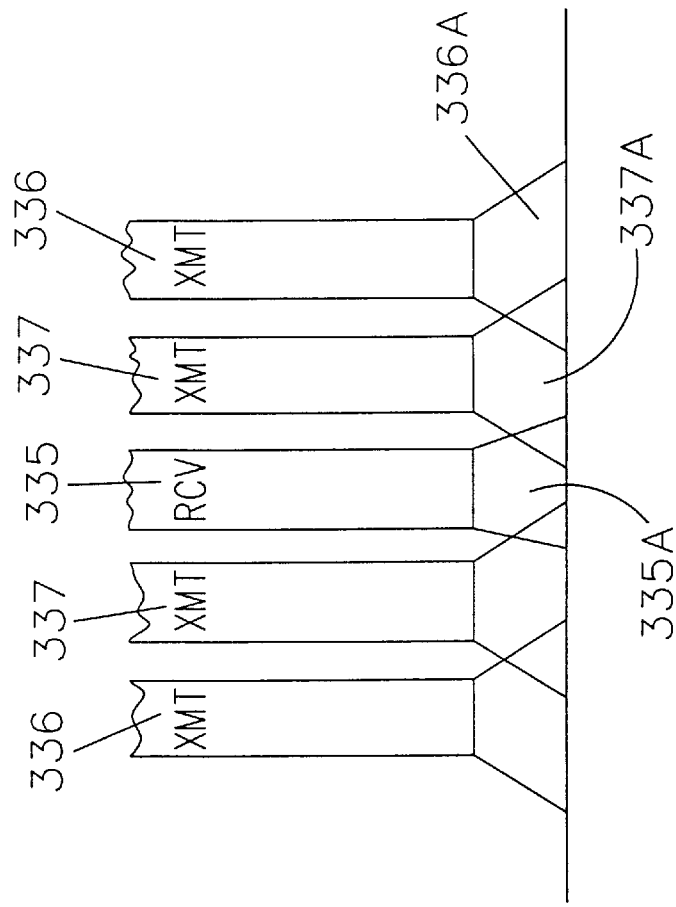
FIG. 15 is a diagram showing transmit and receiving fiber optics of a measurement instrument embodying the invention and the path of radiation emitted or received by the fiber optics.

FIG. 15 shows a receive optical fiber 335 and four transmit optical fibers 336 and 337 surrounding the receive optical fiber 335. The receive optical fiber has a smaller numerical aperture than the transmit optical fibers. The lines extending down from the bottom of the optical fibers show the path that radiation would take to leave or enter the optical fibers. For instance the area 335A shows the path that radiation may take to enter the receive optical fiber 335. The areas marked 336A and 337A show the path that radiation may take when leaving a transmit optical fiber 336 and 337. Typically, the numerical aperture of the receive optical fiber 335 will be smaller than the numerical aperture of the transmit optical fibers 336 and 337.

Bilirubin Measurement Process

Bilirubin can be measured in the aqueous of a patient's eye, or the sclera (white) of the eye, based on a fluorescent signature. Reflectance measurements can also be made on the tympanic membrane of the patient's ear. Finally, reflectance/scattering based measurements can be made on a patient's skin.

Current literature has indicted that the aqueous levels are likely to yield the same results as serum levels of albumin bound bilirubin. However, measurements on five jaundiced adults showed very low signal levels. Direct measurements in the aqueous are also difficult due to low signal levels. This is probably due to the photoconversion taking place in that location, i.e., too much light is allowed into the aqueous in a typical person. There are also difficulties in the evaluation due to human factors (such as the fact that infants may not stare in a particular direction for an extended period of time). Consequently, direct measurement in the aqueous is not preferred due to the low signal-to-noise ratio and poor human factors.

Direct measurements in the sclera is advantageous in that the yellow color is clearly visible, and hence the presence of bilirubin is obvious. Also, this approach is advantageous over a skin based measurement because it avoids the issue of variations in skin color or thickness. This approach was tested on five jaundiced adults. The approach yielded good signal levels, unlike the measurements in the aqueous, however, repeatability was not very good. Also, data indicated a type of photobleaching affect from the excitation light, even during the data collection interval. Spatial distribution was also not constant due, among other things, to eyelid shading. Finally, measurements on subjects shifted dramatically after those subjects spent some time outside compared to measurements taken before those subjects went outside. Consequently, direct measurement in the sclera, although yielding a high signal-to-noise ratio, is not very repeatable and encounters poor human factors.

Direct measurements on the tympanic membrane suffers from several shortcomings including poor vascularization, difficulty in determining levels of bilirubin in the membrane, and poor human factors, particularly on premature babies.

Reflectance/scattering cutaneous measurements seem to be the most promising non-invasive approach to measuring bilirubin. Also, cutaneous measurements provide a simple interface with which to work.

U.S. Pat. No. 5,353,790, the contents of which are incorporated herein by reference, presents a method and apparatus for determining bilirubin concentration in human tissue such as skin. In particular, the patent discusses reflecting light from the skin of a patient to determine a bilirubin concentration. The approach corrects for maturity-dependent optical properties of the skin, including the amount of melanin in the skin and the amount of blood in the skin. Reflected red to infrared light is used to determine the maturity-dependent optical properties, reflected red light is used to determine melanin content, and reflected yellow-orange light is used to determine the amount of blood in the skin. These quantities are used, in combination with reflected blue light, to calculate cutaneous bilirubin concentration.

U.S. Pat. No. 5,353,790 discusses the absorption spectrum of melanin and shows that the melanin absorption spectra essentially decreases linearly with wavelength in the visible region. Moreover, since the melanin absorption varies orders of magnitudes over the visible region, variations in skin pigmentation will cause large absolute changes in the absorption at the shorter wavelengths, but the same magnitude changes will cause relatively minuscule absolute changes in the very long wavelengths (>800 nm). The melanin pigmentation measured in the far red wavelength range was found to have a pivot point at around 637 nm.

A bilirubin measurement system takes advantage of the above phenomena and uses spectral reflectance to determine a serum bilirubin level in mg/dL (milligrams of bilirubin per deciliters of blood), as will now be discussed.

Figure 10:
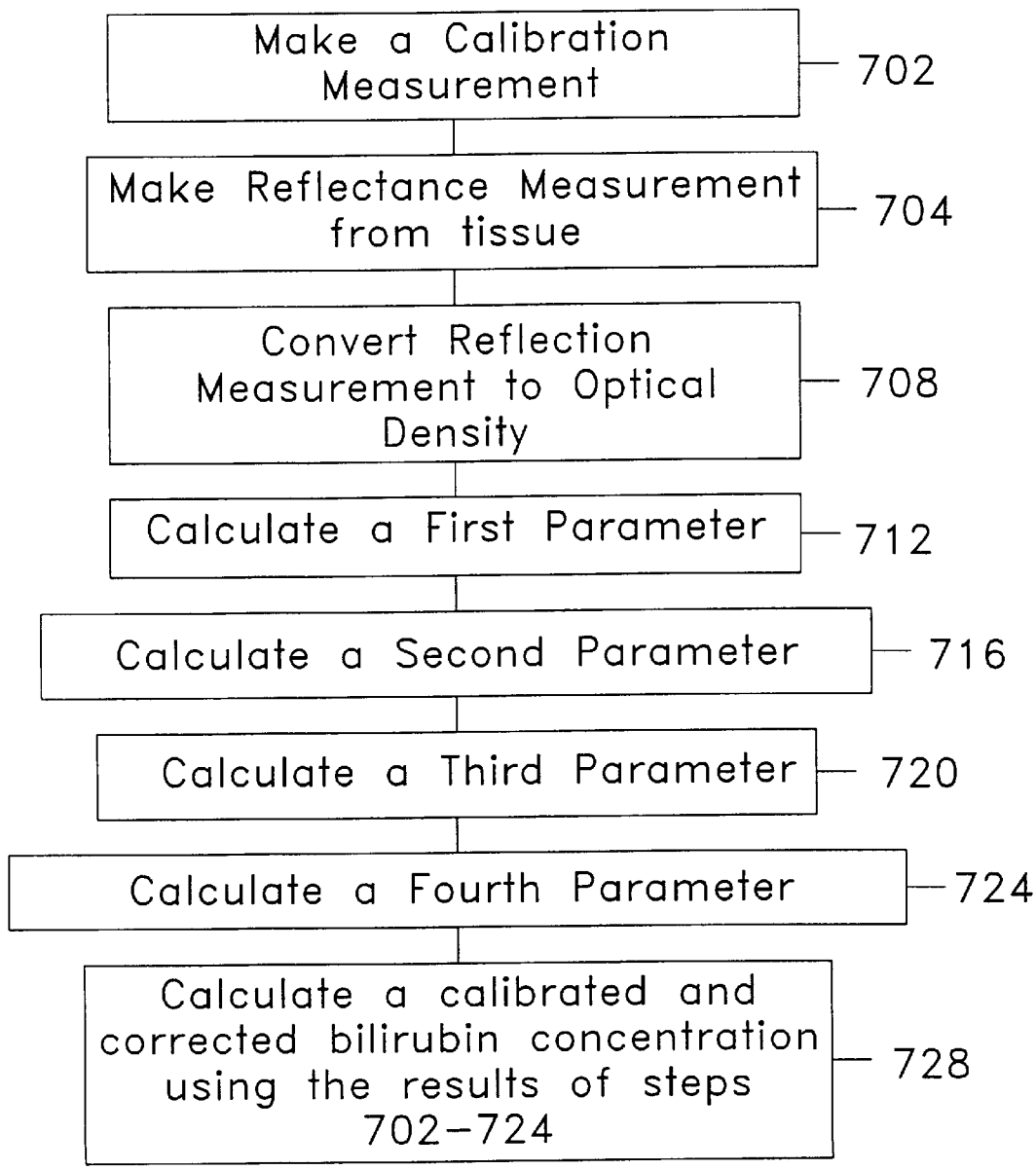
FIG. 10 is a flowchart of a method of performing bilirubin measurements on a patient.

FIG. 10 shows a flowchart setting forth the steps of a first method embodying the invention that may be used by a measurement system to perform bilirubin measurements on a patient. The steps performed are an improved version of the approach discussed in U.S. Pat. No. 5,353,790. Step 702 involves performing a calibration measurement in a manner similar to that described above with reference to FIG. 3E. This involves simply outputting radiation to a calibration target, and measuring the return signal (due to reflection where reflection is meant to include any type of scattering). The calibration measurement yields a measured calibration spectrum, which is compared to an expected calibration spectrum (which in turn, depends on the material of surface 41). The difference between the expected or known spectrum and the measured spectrum serves as the calibration data. The calibration data is used to modify actual measured data, thereby compensating for unit to unit and time varying changes in source luminosity, delivery optics, collection optics, detection sensitivity, electronic drift, and environmental conditions such as temperature and humidity.

Step 704 involves making a measurement of a patient's skin by illuminating the skin with light and detecting a frequency spectrum of light reflected from the patient's skin. Step 708 involves converting the reflection (scattering) measurements into an optical density. Step 712 then involves calculating, from a first portion of the spectrum, a first parameter indicative of a maturity of the skin. Step 716 involves calculating, from a second portion of the spectrum, a second parameter indicative of an amount of melanin in the skin. Step 720 involves calculating, from a third portion of the spectrum, a third parameter indicative of a blood content of the skin. Step 724 involves calculating, from a fourth portion of the spectrum, a fourth parameter indicative of an uncorrected bilirubin concentration in the skin. Step 728 involves calculating a corrected bilirubin concentration in the skin as a function of the first, second, third and fourth parameters.

Figure 11:
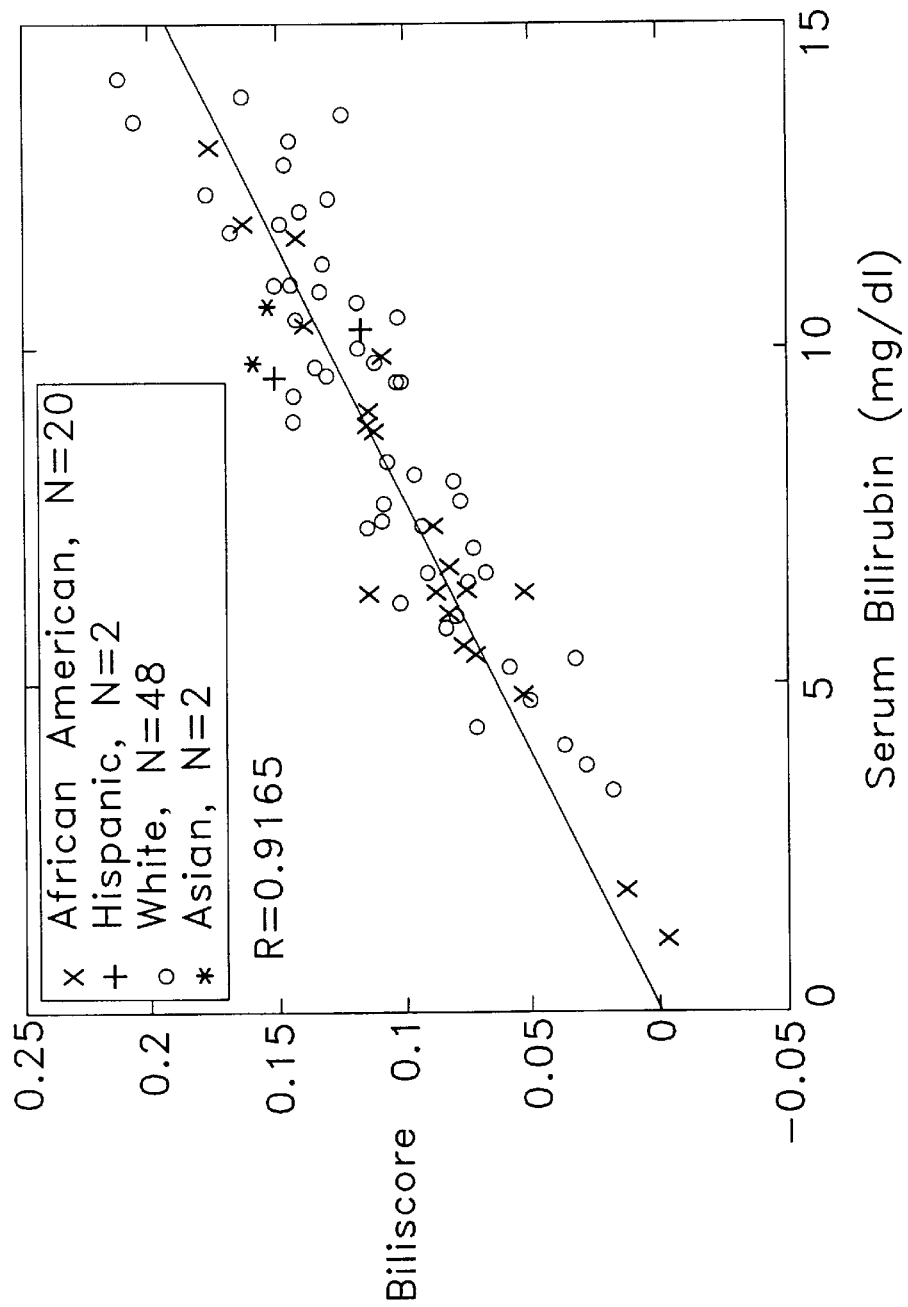
FIG. 11 is a diagram showing the results of data taken using the method of FIG. 10 versus a standard serum bilirubin (heel stick) method.

FIG. 11 shows the results of data taken using the method illustrated in FIG. 10, versus a standard serum bilirubin (heel stick) method. The subjects were 72 full term babies of varied ethnic background, with 20 African Americans, 2 Hispanic Americans, 48 white Americans, and 2 Asian Americans. "R" represents the correlation coefficient between the measurement method described in FIG. 10, versus the standard method of serum bilirubin. The correlation coefficient shown is 0.9165 with a perfect correlation given as 1.0000. The tests represent a purely prospective application of the method illustrated in FIG. 10.

Figure 18:
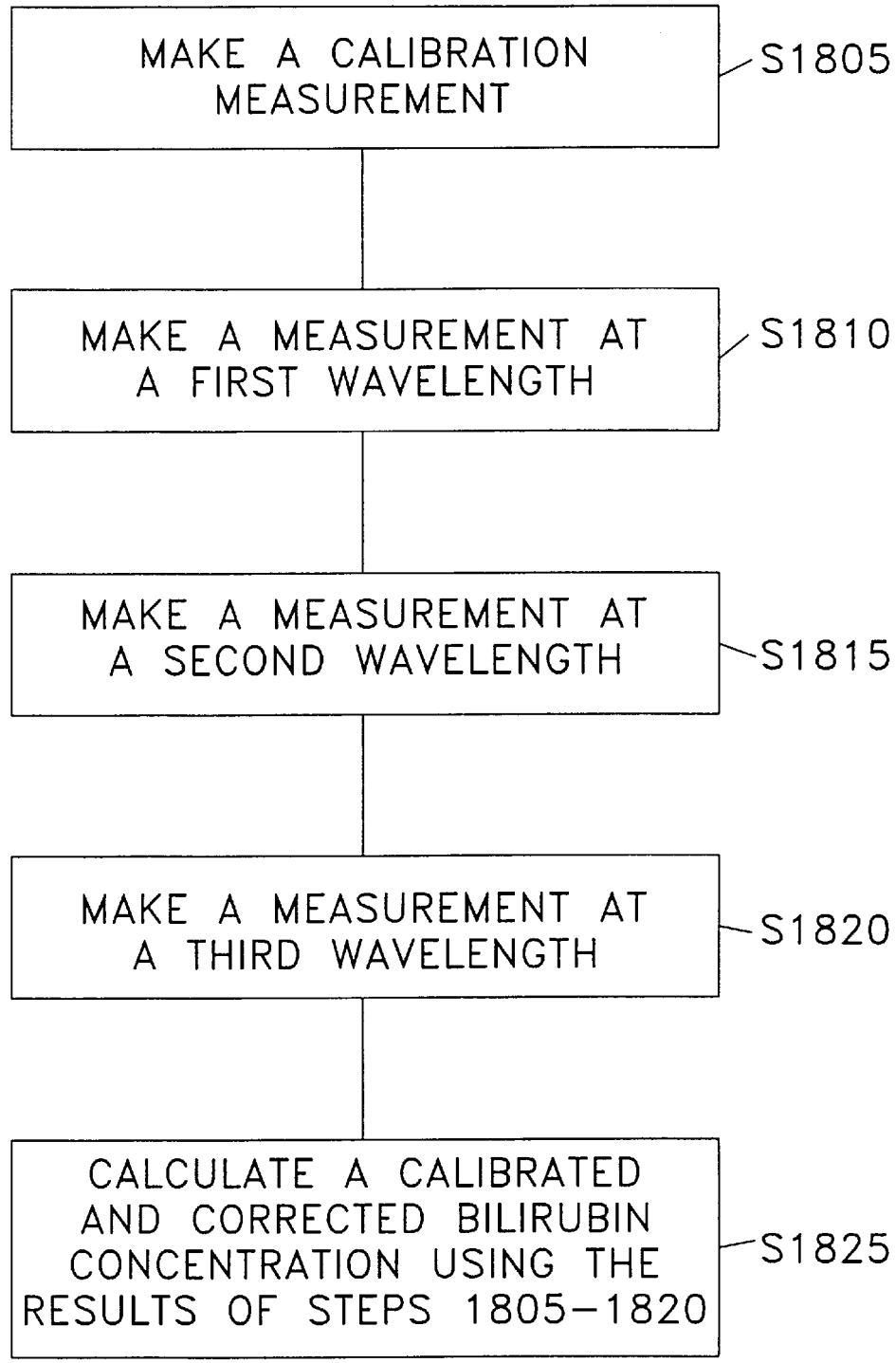
FIG. 18 is a flow chart showing the steps of a method embodying the invention for calculating bilirubin concentration of a patient.

FIG. 18 shows a flowchart setting forth the steps of another method embodying the invention for measuring a bilirubin concentration of a patient. This second method is a more simplified method compared to the method described above.

In step 1805 the measurement system first makes a calibration measurement as described above. Next, in step S1810, a measurement is made using a first portion of the spectrum to determine an amplitude of the reflected light at a first wavelength. Next, in step S1815, a measurement is made at a second portion of the spectrum to determine an amplitude of light at a second wavelength. The first and second wavelengths are indicative of the blood content of the patient's skin. In step 1820, a third measurement is made to determine the amplitude of the reflective light at a third wavelength indicative of an uncorrected bilirubin score. In step S1825, a CPU of the measurement device calculates a calibrated and corrected bilirubin concentration using the results of steps 1805 through 1820.

Figure 20:
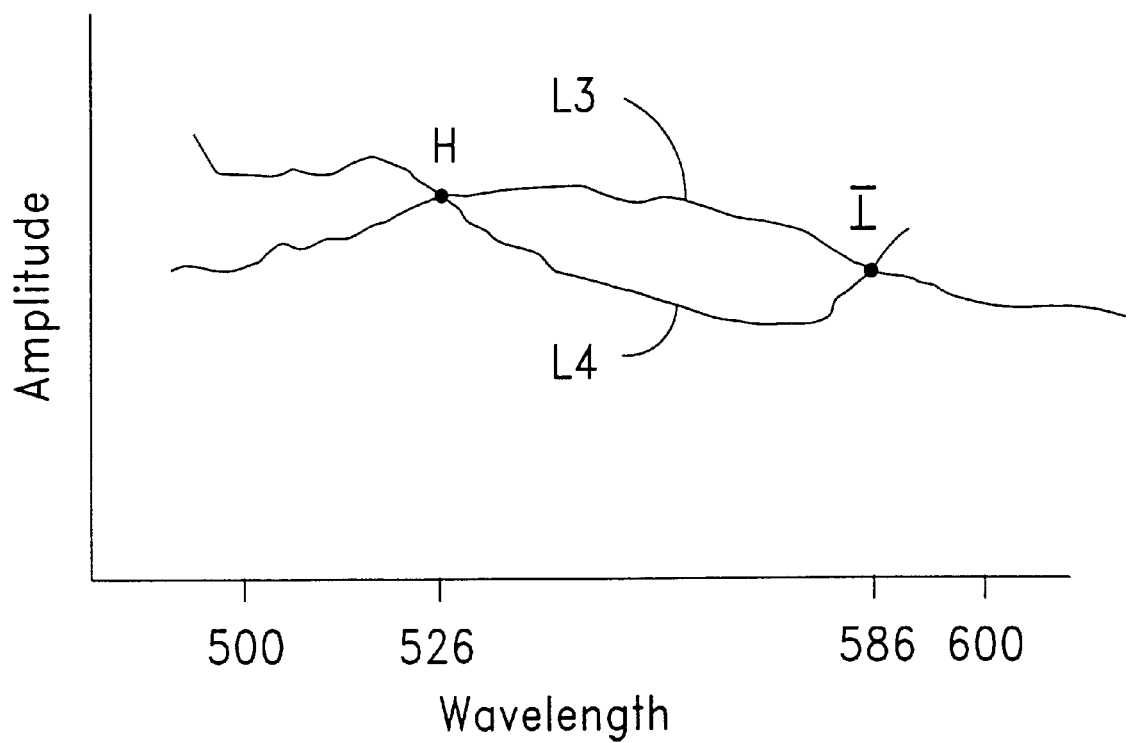
FIG. 20 is a diagram showing the amplitude of light reflected from a patient's skin under two conditions, the first condition corresponding to blood in the patient's skin being 100% oxygenated and the second condition corresponding to the blood in the patient's skin having no oxygen.

The significance of making measurements at the first and second wavelengths will now be explained with reference to FIG. 20. FIG. 20 illustrates two lines, L3 and L4, that represent the amplitude of light reflected from a patient's skin under two different conditions. In a first condition, the blood flowing through the patient's skin is fully oxygenated. In the second condition, the blood flowing through the patient's skin has no oxygen attached to the hemoglobin in the blood. As shown in FIG. 20, lines L3 and L4 cross one another at two points H and I. Experimental results have indicated that the wavelengths corresponding to points H and I are at approximately 526 and 585 nanometers, respectively.

By making the measurements of the amplitude of light reflected from a patient's skin at approximately 526 nanometers and 586 nanometers, it is possible to obtain a measurement representative of the blood content of the patient's skin. Because the measurements are made at the crossover points, it does not matter whether the blood in the patient's skin is fully or partially oxygenated.

Figure 16:
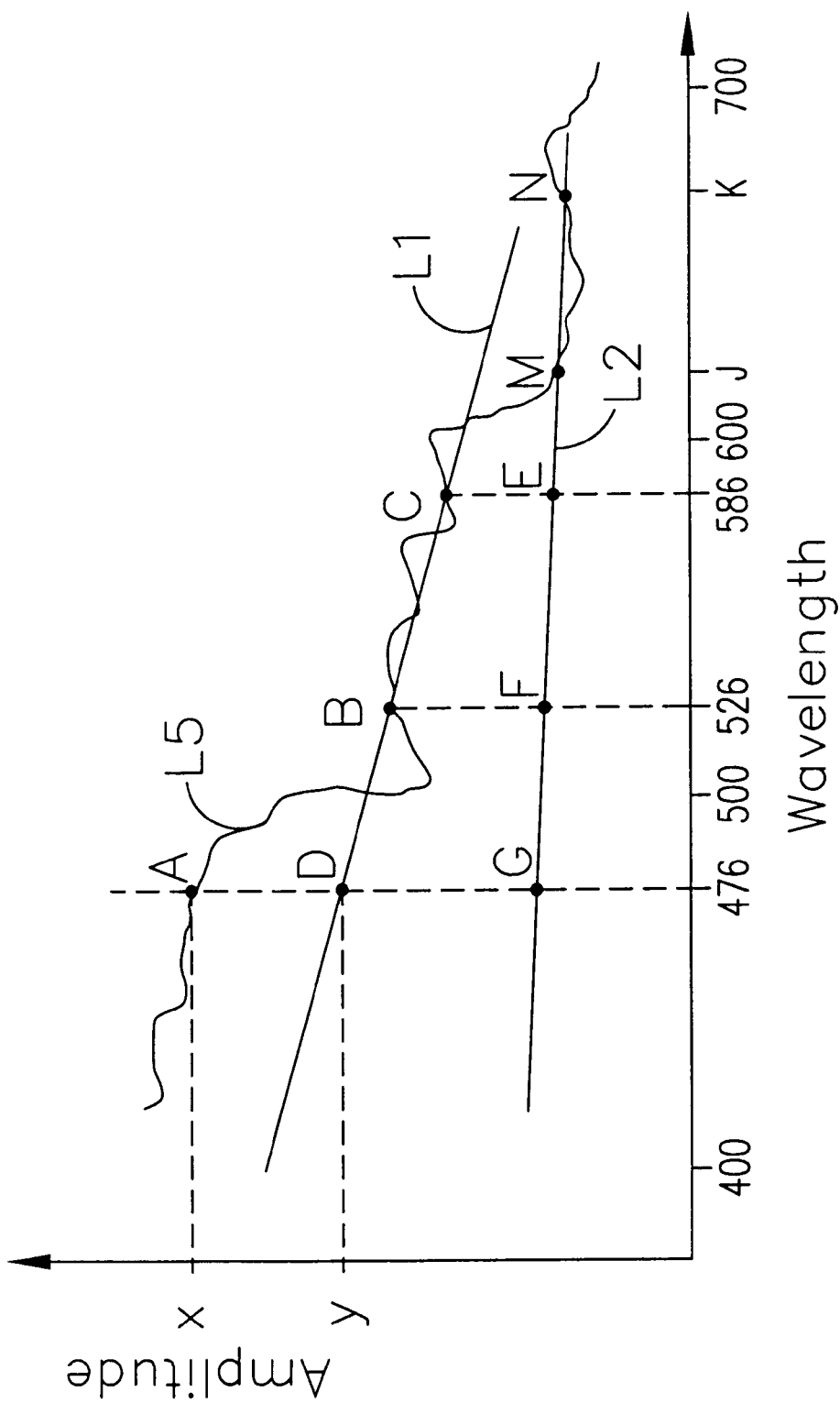
FIG. 16 is a diagram showing the amplitude of radiation reflected or scattered from a patient's skin for explaining how a corrected bilirubin concentration is calculated using a method embodying the invention.

The method of calculating a calibrated and corrected bilirubin concentration of FIG. 18 will now be further explained with reference to FIG. 16. In FIG. 16, L5 represents an amplitude of light reflected from a patient's skin at various wavelengths.

The amplitude of light reflected from a patient's skin at a first wavelength, as measured in step 1810, is taken at a wavelength of approximately 526 nanometers. The amplitude at this wavelength is represented by point B in FIG. 16. The amplitude of the light reflected from the patient's skin at the second wavelength is taken at approximately 586 nanometers, which is represented by point C in FIG. 16. An imaginary line L1 is drawn through points B and C and backwards through smaller wavelengths of the visible light spectrum. The amplitude value at the intersection of the line L1 and an imaginary line at 476 nanometers is then determined, which is represented by point D in FIG. 16. Point A in FIG. 16 represents the measured amplitude of the light reflected from the patient's skin at 476 nanometers. The value of point D is then subtracted from the value of point A to determine a corrected bilirubin score. This corrected bilirubin score is then used with the calibration data taken during a calibration measurement to determine a calibrated and corrected bilirubin concentration of the patient's skin.

The second method described above is far more simple than the first method, as it only involves taking amplitude measurements of reflected light at three discreet wavelengths. Experimental results have shown that the second method provides substantially the same level of accuracy as the first method, and in some cases the second method produces even better results.

A third method of determining a bilirubin concentration in a patient's skin will now be described with reference to FIG.

Figure 19:
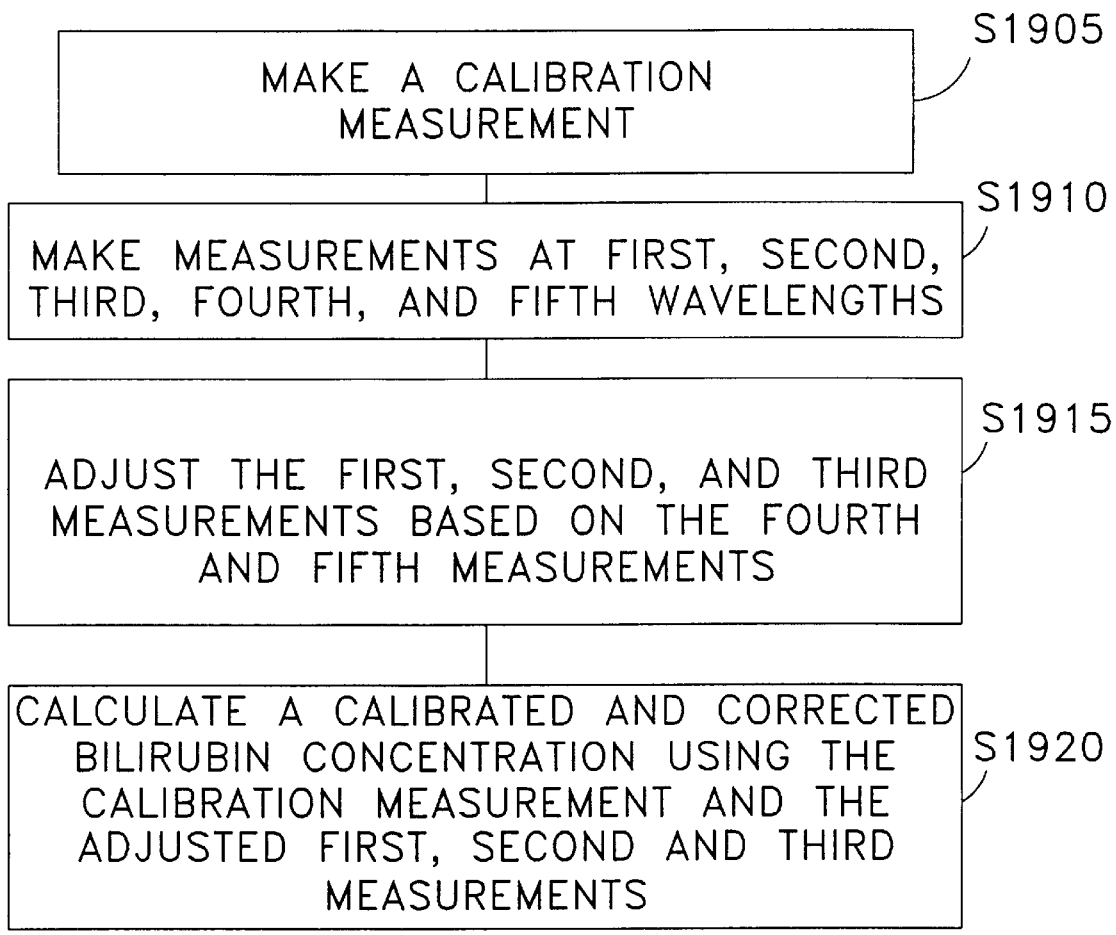
FIG. 19 is a flow chart of another method embodying the invention for calculating a bilirubin concentration of a patient.

19. FIG. 19 shows a flowchart of the steps of a third method of determining a patient's bilirubin concentration. In step 1905, a calibration measurement is taken as described above. In step 1910, measurements of the amplitude of light reflected from a patient's skin are made at first, second, third, fourth and fifth wavelengths. In step 1915, the first, second and third measurements are adjusted based on the fourth and fifth measurements. In step 1920, a calibrated and corrected bilirubin concentration is calculated using the calibration measurement and the adjusted first, second and third measurements.

The first, second and third measurements taken during step S1910 are taken at the wavelengths 486 nanometers, 526 nanometers, and 586 nanometers as described above in connection with the second method. The fourth and fifth measurements are taken at wavelengths J and K, as shown in FIG. 16, which are represented by the points M and N. The wavelengths corresponding to J and K are in the range between 600 and 700 nanometers. The amplitude of the light reflected from the patient's skin at frequencies J and K are representative of melanin in the patient's skin. A line drawn through points J and K will have a negative slope that indicates the amount of melanin in the patient's skin. The greater than negative slope (or the more steeply the line is inclined down toward the right) the greater the amount of melanin.

In step 1915, the first, second and third measurements are adjusted based on the fourth and fifth measurements. To accomplish this adjustment, a line L2 is drawn through points M and N, and the line L2 is projected backwards through the smaller wavelengths, as shown in FIG. 16. Points of intersection of the line L2 with imaginary lines at the first, second and third wavelengths are determined. These points are shown as points E, F and G in FIG. 16. The amplitude values of points E, F and G are then subtracted from the respective measurements made at these wavelengths, which are shown as points C, B and A. These adjusted measurements for the first, second and third wavelengths are then used to determine a calibrated and corrected bilirubin concentration for the patient according to the methods described above.

Many alternatives and modifications of the above examples would be apparent to those skilled in the art upon reading the foregoing or practicing the invention. The apparatus and methods described above are intended to be exemplary and are not intended to limit the scope of the invention as defined by the following claims.

What is claimed is:

1. A method for determining a bilirubin concentration in a mammal, comprising the steps of:
    a) illuminating a portion of a skin of the mammal with light;
    b) detecting a frequency spectrum of light scattered from the skin;
    c) determining, from first and second portions of the spectrum, a first parameter indicative of a blood oxygen content of the skin;
    d) determining, from a third portion of the spectrum, a second parameter indicative of an uncorrected bilirubin concentration; and
    e) calculating a corrected bilirubin concentration based on the first and second parameters.

2. The method of claim 1, further comprising the step of performing a calibration measurement on a calibration target and storing resulting calibration data prior to illuminating the mammal's skin with light, wherein the step of calculating a corrected bilirubin concentration is also based on the calibration data.

3. The method of claim 1, wherein the first and second portions of the spectrum are at approximately 520 nm and 585 nm, respectively.

4. The method of claim 3, wherein the third portion of the spectrum is at approximately 476 nm.

5. The method of claim 1, wherein the third portion of the spectrum is at approximately 476 nm.

6. The method of claim 1, wherein the performance of steps a–e result in a first corrected bilirubin concentration, further comprising the steps of:
    f) repeating steps a–e to calculate a second corrected bilirubin concentration; and
    g) calculating an average corrected bilirubin concentration based on the first and second corrected bilirubin concentrations.

7. The method of claim 6, wherein different portions of the mammal's skin are illuminated each time steps a–e are performed.

8. The method of claim 7, wherein the different portions of the mammal's skin are located on different portions of the mammal's body.

9. The method of claim 1, wherein the performance of steps a–e result in a first corrected bilirubin concentration, further comprising the steps of:
    f) repeating steps a–e at least twice to calculate at least second and third corrected bilirubin concentrations;
    g) calculating an average corrected bilirubin concentration and a standard deviation using at least the first, second and third corrected bilirubin concentrations;
    h) comparing the calculated standard deviation to a predetermined maximum standard deviation; and
    i) repeating steps a–g if the calculated standard deviation exceeds the predetermined maximum standard deviation.

10. A system for determining a bilirubin concentration in a mammal, comprising:
    means for illuminating a portion of the mammal's skin with light;
    means for detecting a frequency spectrum of light scattered from the skin;
    means for determining, from first and second portions of the spectrum, a first parameter indicative of a blood content of the skin;
    means for determining, from a third portion of the spectrum, a second parameter indicative of an uncorrected bilirubin concentration; and
    means for calculating a corrected bilirubin concentration based on the first and second parameters.

11. The system of claim 10, further comprising:
    means for performing a calibration measurement on a calibration target and for storing resulting calibration data, wherein the means for calculating a corrected bilirubin concentration also utilizes the calibration data.

12. The system of claim 10, further comprising:
    means for calculating an average corrected bilirubin concentration and a standard deviation using at least three calculated corrected bilirubin concentrations; and
    means for comparing the calculated standard deviation to a predetermined maximum standard deviation.

13. The system of claim 10, further comprising means for holding a removable calibration target that can be used to calibrate the system prior to determining the bilirubin concentration of a mammal.

14. The system of claim 13, further comprising a removable calibration target mounted on the calibration target holding means.

15. The system of claim 14, wherein the removable calibration target comprises structure that remains attached to the calibration target holding means after a portion of the removable calibration target is removed to allow a measurement to be made.

16. A system for measuring a bilirubin concentration of a mammal by directing radiation onto a portion of a skin of the mammal and analyzing scattered or reflected radiation returning from the skin, comprising:

a radiation analyzing device for analyzing scattered or reflected radiation and for outputting radiation data;

a radiation source;

at least one radiation transmitting conduit for directing radiation from the radiation source to a portion of the mammal's skin;

at least one radiation receiving conduit for directing radiation scattered or reflected from the mammal's skin to the radiation analyzing device; and means for calculating a bilirubin concentration of the mammal based on an amplitude of the reflected or scattered radiation at first and second wavelengths indicative of a blood content of the mammal's skin and on an amplitude of the reflected or scattered radiation at a third wavelength indicative of a bilirubin concentration in the mammal's skin.

17. The system of claim 16, wherein the at least one radiation transmitting conduit directs radiation at the mammal's skin at acute angle relative to an axis perpendicular to the skin surface.

18. The system of claim 17, wherein the angle is approximately twelve degrees.

19. The system of claim 17, wherein the angle is large enough to reduce radiation backscattering.

20. The system of claim 16, wherein the at least one radiation transmitting conduit comprises a plurality of radiation transmitting conduits, and wherein the at least one radiation receiving conduit is surrounded by the plurality of radiation transmitting conduits.

21. The system of claim 20, wherein the plurality of radiation transmitting conduits are arranged in first and second annular rings, the first annular ring surrounding the at least one radiation receiving conduit, and the second annular ring surrounding the at least one radiation receiving conduit and the first annular ring.

22. The system of claim 16, wherein a numerical aperture of the at least one radiation transmitting conduit is matched to the radiation source, and wherein a numerical aperture of the at least one radiation receiving conduit is matched to the radiation analyzing device.

23. The system of claim 22, wherein the numerical aperture of the at least one radiation transmitting conduit is different from the numerical aperture of the at least one radiation receiving conduit.

24. The system of claim 16, further comprising a window located between the radiation transmitting and receiving conduits and an exterior measuring end of the system, wherein the window comprises a soft polymer that acts as an index matching agent between the radiation transmitting and receiving conduits and the mammal's skin.

25. The system of claim 16, wherein a length of the at least one radiation receiving conduit is sufficiently long such that mode scrambling occurs.

26. The system of claim 16, further comprising a proximity sensing device for sensing a proximity of a distal end of the radiation transmitting and receiving conduits to the mammal's skin.

27. The system of claim 26, wherein the system only measures the condition of the mammal when the proximity sensing device indicates that the radiation transmitting and receiving conduits are within a predetermined proximity to the mammal's skin.

28. The system of claim 26, wherein the proximity sensing device comprises a spring loaded annulus that surrounds the radiation transmitting and receiving conduits.

29. The system of claim 16, further comprising a transmitter for transmitting data regarding the calculated condition of the mammal to a remote recording device.

30. The system of claim 29, wherein the transmitter comprises an infrared transmitter.

31. The system of claim 16, wherein the radiation analyzing device comprises a spectrometer.

32. The system of claim 16, wherein the radiation analyzing device comprises a diffraction grating and a plurality of detectors, wherein the diffraction grating focuses radiation having predetermined wavelengths on respective ones of the plurality of detectors.

33. The system of claim 16, wherein the radiation analyzing device comprises at least one radiation detector and a plurality of radiation filters, each of the plurality of radiation filters allowing only a narrow wavelength band of radiation to reach the at least one radiation detector.

34. The system of claim 16, wherein the radiation analyzing device comprises a radiation detector and a linear variable filter for allowing selected wavelengths of radiation to reach the radiation detector.

35. A method of measuring a condition of a mammal with a device that outputs radiation from a distal end of the device, comprising the steps of:

applying an index matching agent to one of a skin of the mammal and the distal end of the device;

emitting radiation from the distal end of the device so that the radiation passes through the index matching agent and is scattered or reflected by the mammal's skin;

receiving the scattered or reflected radiation at the distal end of the device; and analyzing the received radiation to determine the condition of the mammal.

36. The method of claim 35, further comprising the step of performing a calibration measurement on a calibration target and storing resulting calibration data prior to the step of emitting radiation so that the radiation is scattered or reflected by the mammal's skin.

37. The method of claim 36, wherein the step of performing a calibration measurement comprises the steps of:

emitting radiation from the distal end of the device so that it is scattered or reflected from the calibration target;

receiving the scattered or reflected radiation at the distal end of the device;

calculating calibration data based on the received radiation; and storing the calibration data.

38. The method of claim 37, wherein the step of applying an index matching agent is performed before the calibration measurement is performed.

39. A calibration device for calibrating a measuring system that transmits radiation to a material or tissue from an output end to effect measurements, comprising:

a removable calibration target;

a structure for holding the removable calibration target, the structure including an opening through which radiation can be transmitted; and an index matching agent for interposition between the output end of the measuring system and the material or tissue being measured.

40. The calibration device of claim 39, wherein the index matching agent comprises a window of a soft polymer that is attached to the structure.

41. The calibration device of claim 39, further comprising a window attached to the structure.

42. The calibration device of claim 41, wherein a substance held within the structure acts an index matching agent between the output end of the measuring system and the removable calibration target while the calibration target is attached to the structure, and wherein the substance acts as an index matching agent between the output end of the measuring system and a material or tissue being measured when the removable calibration target is removed.

43. The calibration device of claim 39, wherein the index matching agent is a gel held within the structure.

44. The calibration device of claim 39, wherein the removable calibration target comprises a user removable tear tab.

45. A method for determining a bilirubin concentration in a mammal, comprising the steps of:

a) illuminating a portion of a skin of the mammal with light;

b) detecting a frequency spectrum of light scattered from the skin;

c) determining, from first and second portions of the spectrum, a first parameter indicative of a blood content of the skin;

d) determining, from third and fourth portions of the spectrum, a second parameter indicative of a melanin content of the mammal's skin;

e) determining, from a fifth portion of the spectrum, a third parameter to indicative of an uncorrected bilirubin concentration; and f) calculating a corrected bilirubin concentration based on the first, second and third parameters.

46. The method of claim 45, further comprising the step of performing a calibration measurement on a calibration target and storing resulting calibration data prior to illuminating the mammal's skin with light, wherein the step of calculating a corrected bilirubin concentration is also based on the calibration data.

47. The method of claim 45, wherein the first and second portions of the spectrum are at approximately 526 nm and 586 nm, respectively.

48. The method of claim 45, wherein the fifth portion of the spectrum is at approximately 476 nm.

49. The method of claim 46, wherein the third and fourth portions of the spectrum are between approximately 600 nm and approximately 700 nm.

* * * * *